United States Patent
Kamiya et al.

(10) Patent No.: US 11,339,181 B2
(45) Date of Patent: May 24, 2022

(54) CRYSTALLINE FORMS OF A JANUS KINASE INHIBITOR

(71) Applicant: Japan Tobacco Inc., Tokyo (JP)

(72) Inventors: Yukihiro Kamiya, Takatsuki (JP); Noriaki Shimoyama, Takatsuki (JP); Ryuhei Okura, Takatsuki (JP); Satoru Noji, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 16/470,854

(22) PCT Filed: Dec. 20, 2017

(86) PCT No.: PCT/JP2017/045731
§ 371 (c)(1),
(2) Date: Jun. 18, 2019

(87) PCT Pub. No.: WO2018/117153
PCT Pub. Date: Jun. 28, 2018

(65) Prior Publication Data
US 2020/0017527 A1    Jan. 16, 2020

Related U.S. Application Data

(60) Provisional application No. 62/437,262, filed on Dec. 21, 2016.

(51) Int. Cl.
| A61K 31/519 | (2006.01) |
| A61K 31/407 | (2006.01) |
| C07D 519/00 | (2006.01) |
| C07D 487/10 | (2006.01) |
| A61P 17/06 | (2006.01) |
| A61P 17/14 | (2006.01) |

(52) U.S. Cl.
CPC ........ *C07D 519/00* (2013.01); *C07B 2200/13* (2013.01)

(58) Field of Classification Search
CPC .. A61K 31/519; A61K 31/407; C07D 519/00; C07D 487/10; A61P 17/06; A61P 17/14; C07B 2200/13
USPC ..... 514/409, 414, 412, 265.1; 548/280, 410, 548/453, 455; 544/280
See application file for complete search history.

(56) References Cited

U.S. PATENT DOCUMENTS

2011/0136778 A1    6/2011    Noji et al.

FOREIGN PATENT DOCUMENTS

| AU | 2016289061 | 12/2017 |
| WO | WO2017006968 | 4/2017 |

OTHER PUBLICATIONS

Brittain, "Polymorphism in Pharmaceutical Solids", Marcel and Dekker Inc., 1999, vol. 95, 24 pages.
U.S. Department of Health and Human Services Food and Drug Administration, "ANDAs: Pharmaceutical Solid Polymorphism—Chemistry, Manufacturing and Controls Information", Center for Drug Evaluation and Research, Jul. 2007, 13 pages.
PCT International Search Report and Written Opinion in International Application No. PCT/JP2017/045731, dated Mar. 1, 2018, 13 pages.
PCT International Preliminary Report on Patentability in International Application No. PCT/JP2017/045731, dated Jun. 25, 2019, 9 pages.
Anamika Sharma et al. "Polymorphism in Pharmaceutical Compounds", Jan. 2011, Advancement and Futuristic Conference Trends in Material Science, pp. 39-48, Section 5 on pp. 43-44.
Caira "Crystalline Polymorphism of Organic Compounds", Tropics in Current Chemistry, 1998, 198:163-208.
Hilfker, Rolf, "Polymorphism: in the pharmaceutical industry. 2006." Weinhem: Wiley-VCH Verlag GmbH & Co. KGaA, Ch. 15, section 15.1-15.6, 17 pages.
Rodriguez-Spong et al., "General Principles of Pharmaceutical Solid Polymorphism: A Supramolecular Perspective", Advanced Drug Delivery Reviews, 2004, 56:241-274.
Russian Search Report in RU Appln. No. 201922566, dated Dec. 28, 2021, 2 pages.
Khramkina M.N. Workshop on Organic Synthesis, Chemistry Publishing House, Leningrad Branch, 1977, Chapter III, p. 51-55.
Hilfiker, Rolf. "Polymorphism: in the pharmaceutical industry," 2006. Wiley-VCH Verlag GmbH & Co. KGaA, Weinheim, Section 1.6 on page 15, 1 page.

*Primary Examiner* — Joseph R Kosack
*Assistant Examiner* — Sagar Patel
(74) *Attorney, Agent, or Firm* — Fish & Richardson P.C.

(57) ABSTRACT

The present invention relates to crystalline forms of the Janus kinase (JAK) inhibitor 3-((3S,4R)-3-methyl-6-(7H-pyrrolo [2,3-d]pyrimidin-4-yl)-1,6-diazaspiro[3.4]octan-1-yl)-3-oxopropanenitrile (Compound A), as well as, compositions thereof, methods of their preparation, methods of use thereof and methods of quantitation.

24 Claims, 17 Drawing Sheets

[Fig. 1]
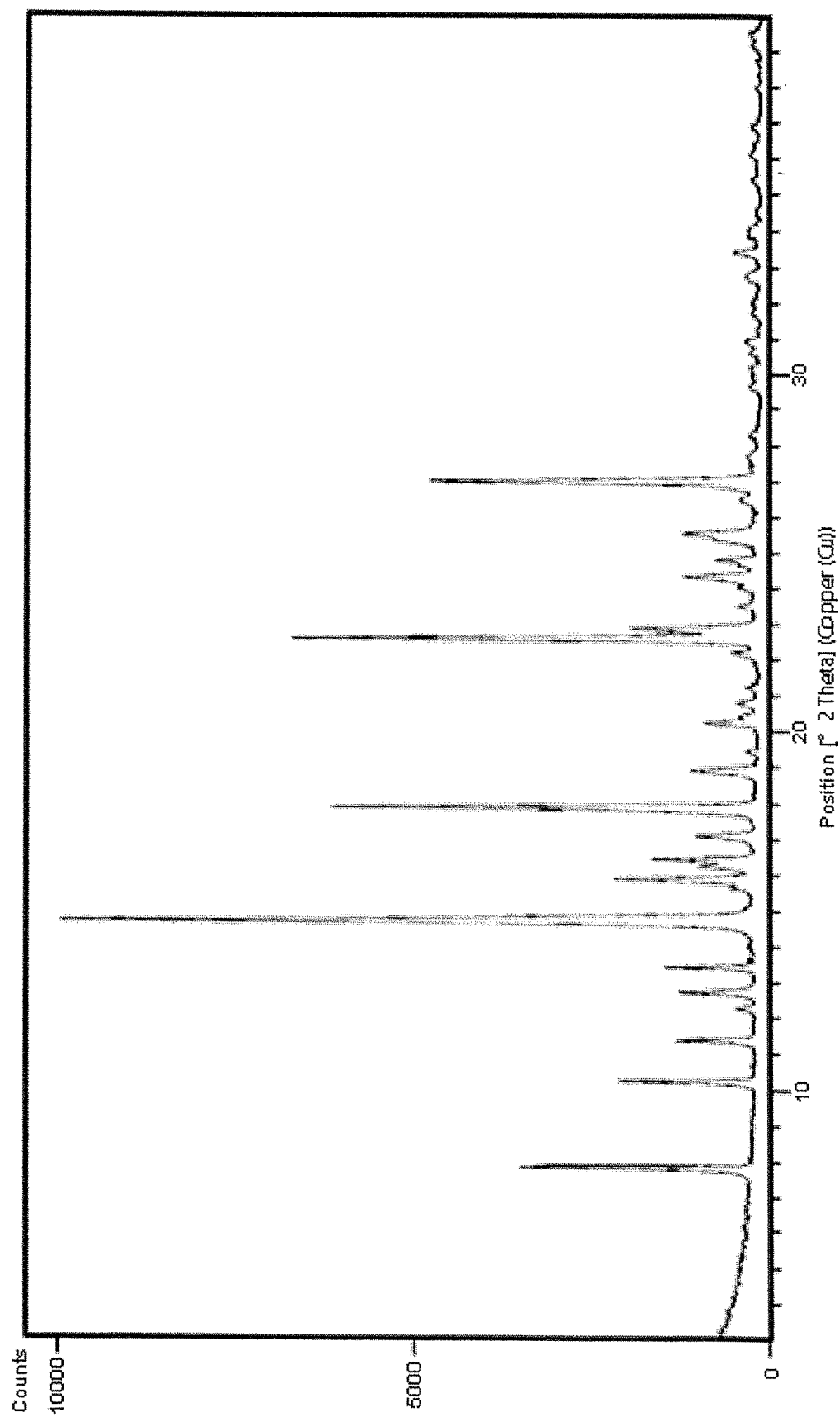

[Fig. 2]
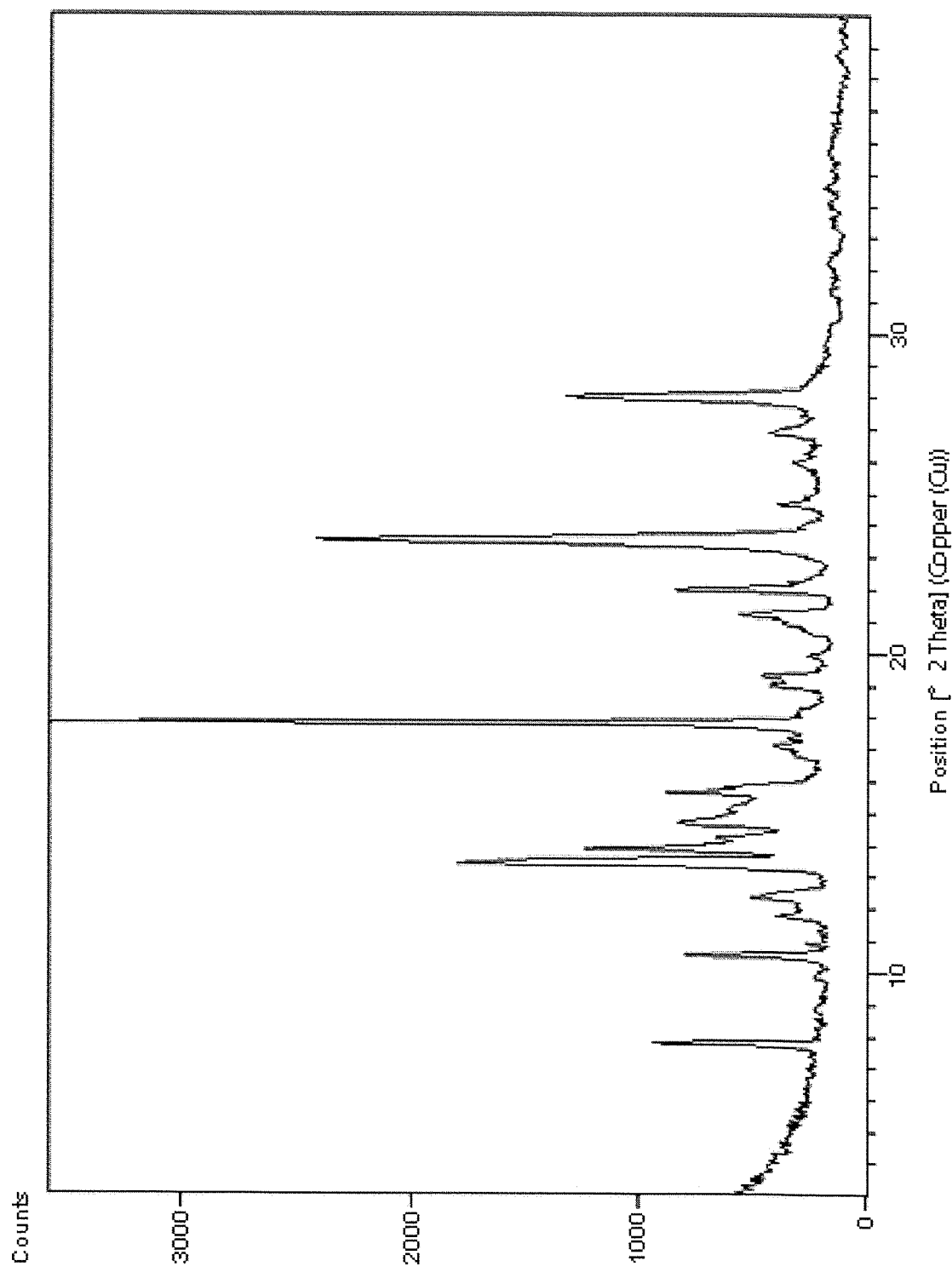

[Fig. 3]
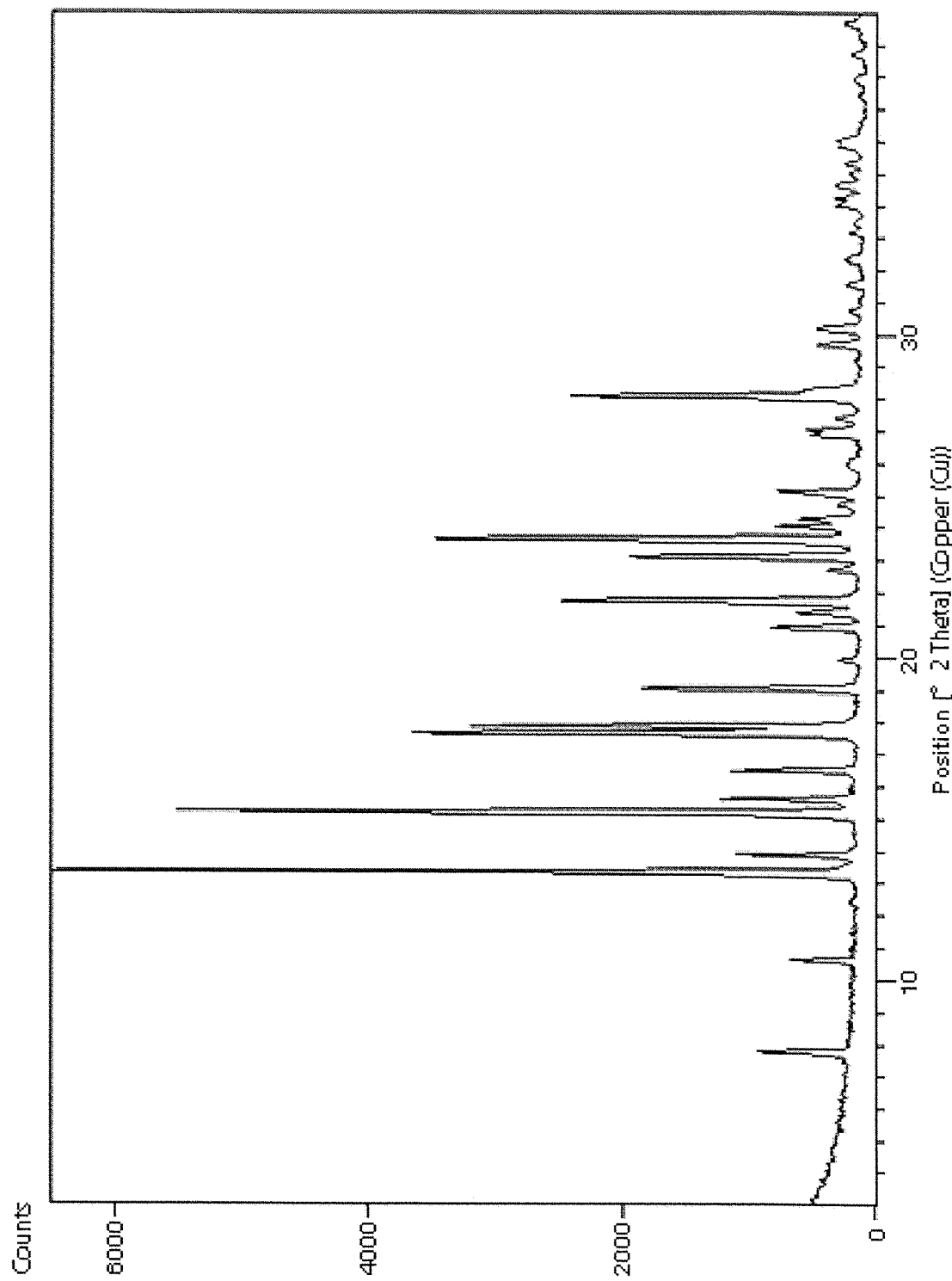

[Fig. 4]
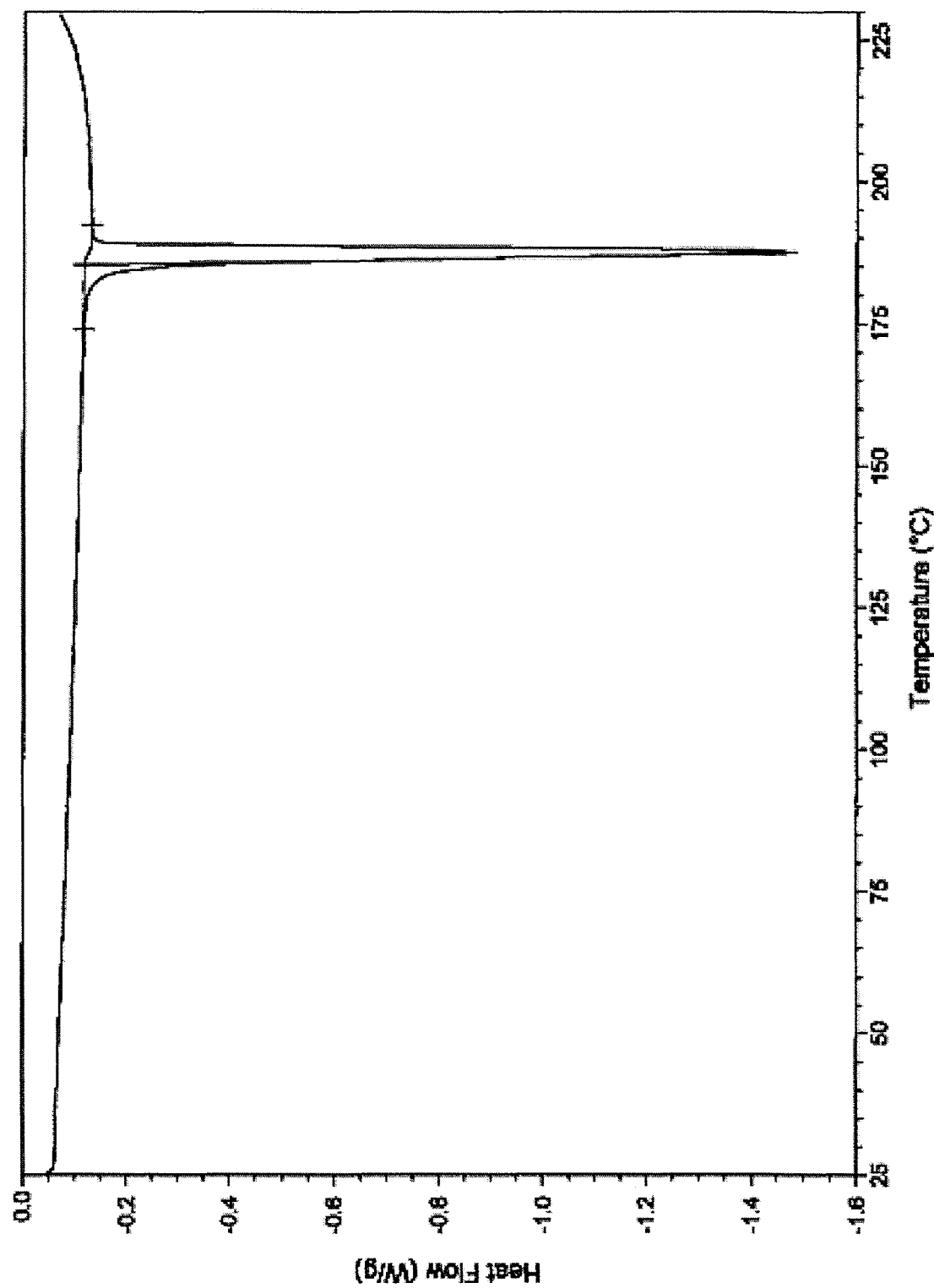

[Fig. 5]
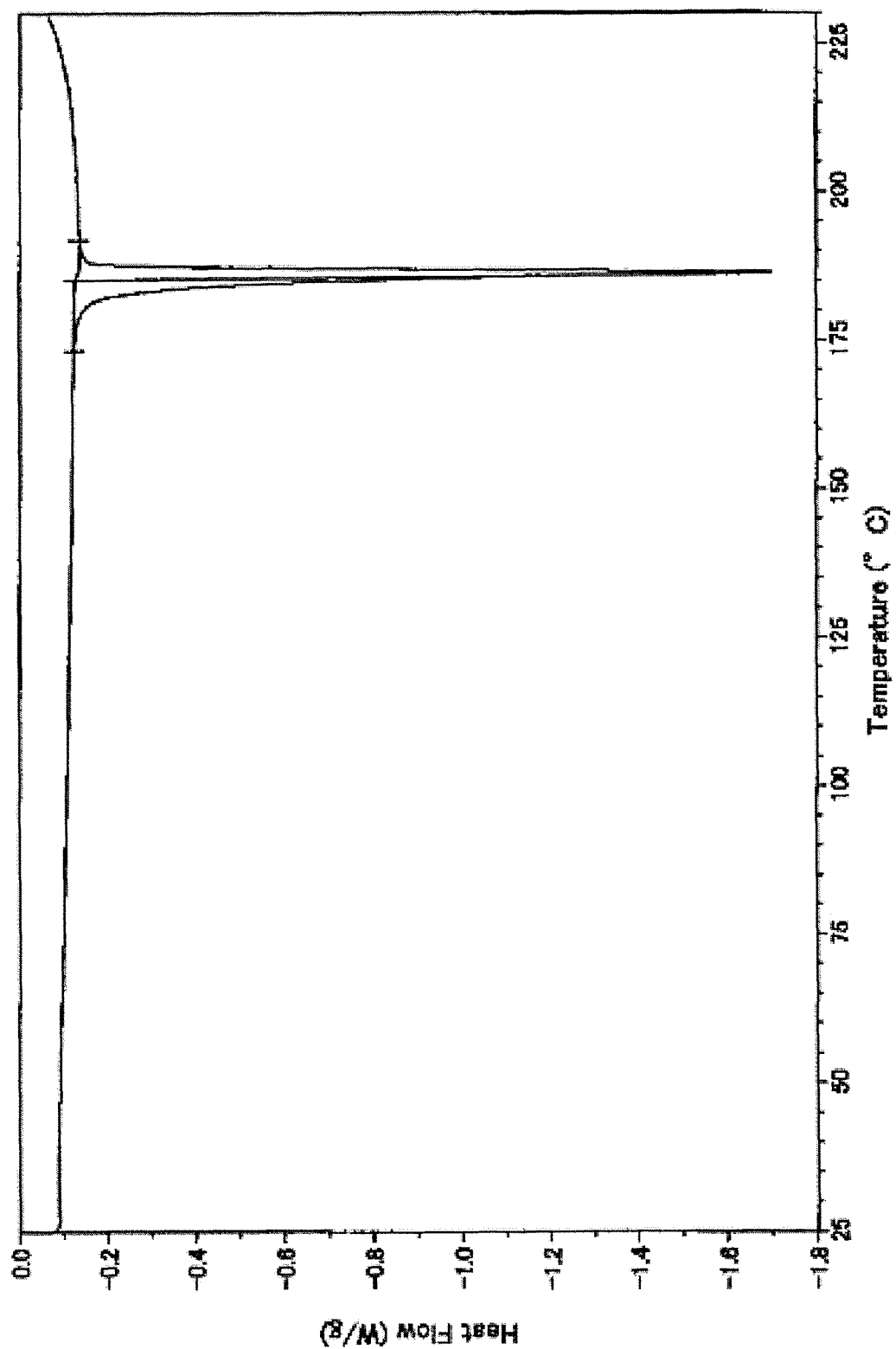

[Fig. 6]
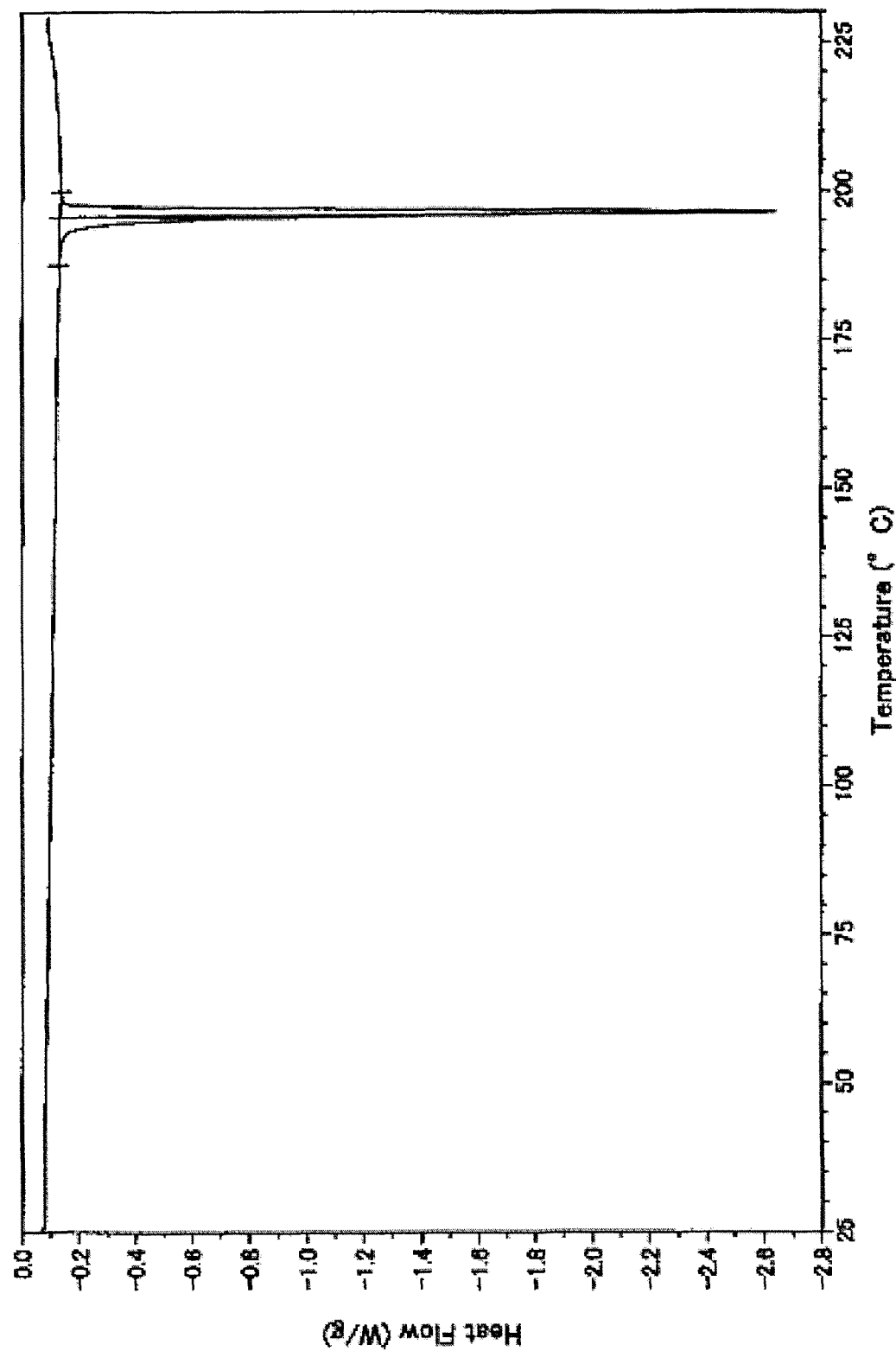

[Fig. 7]
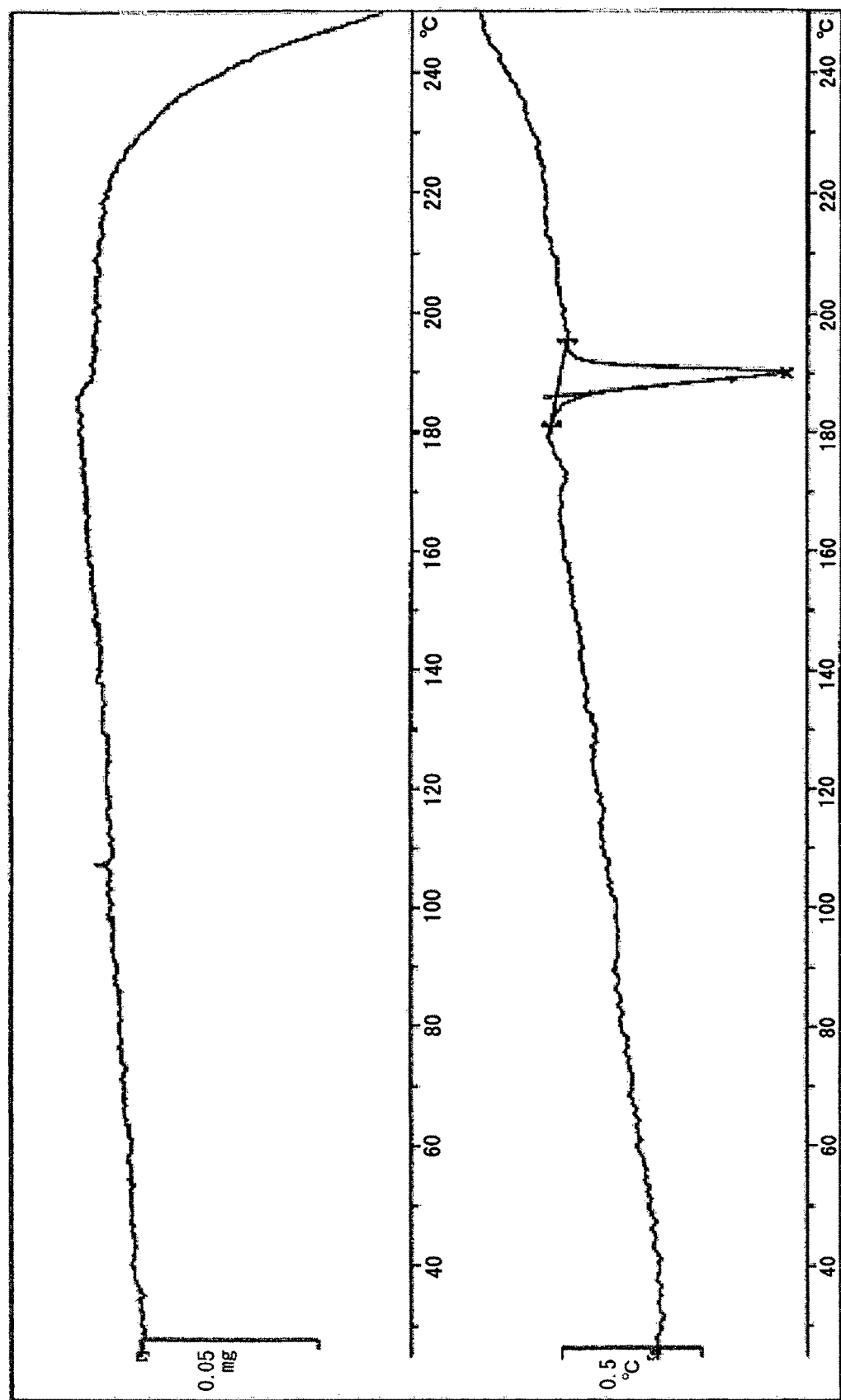

[Fig. 8]
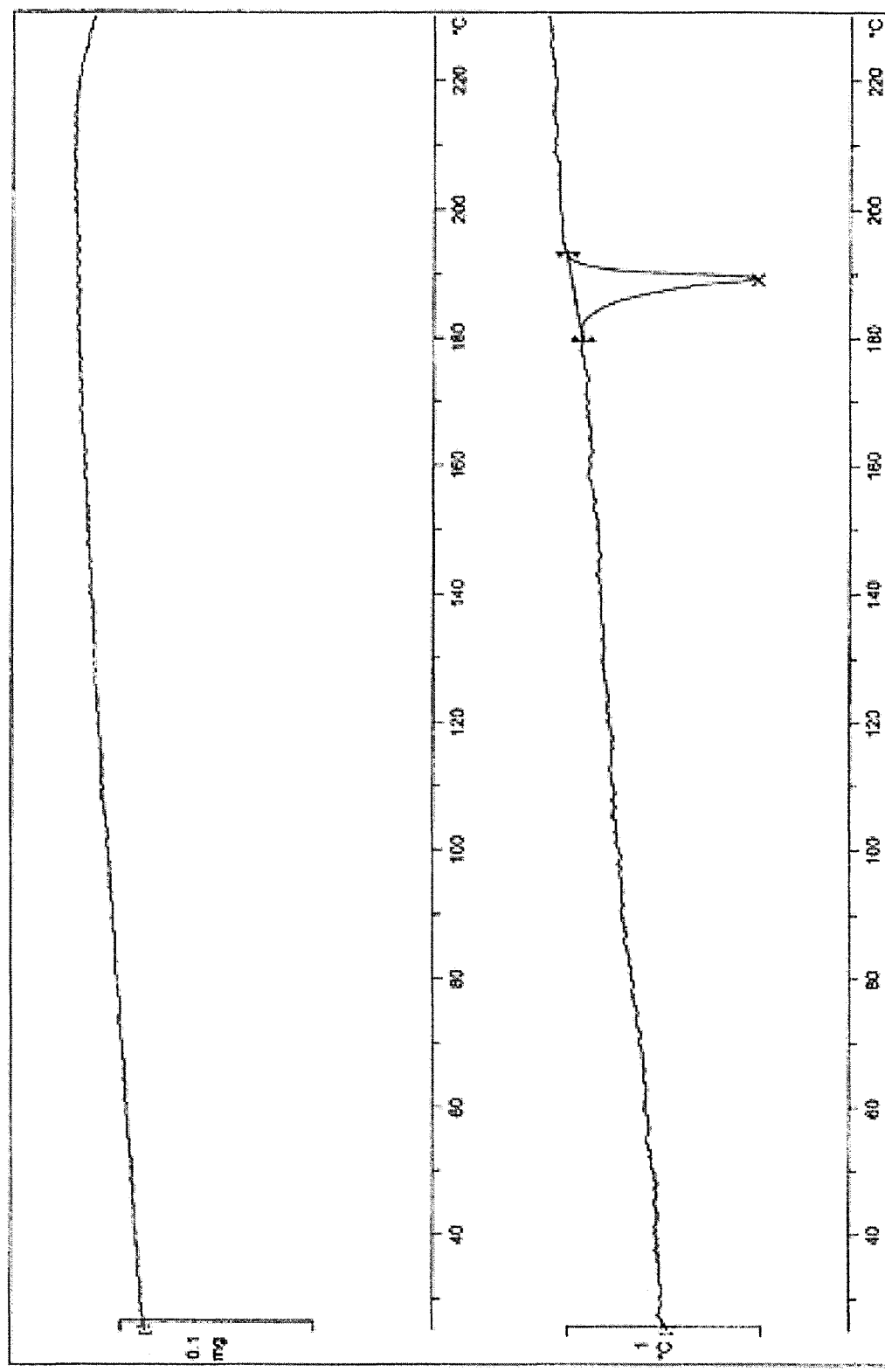

[Fig. 9]
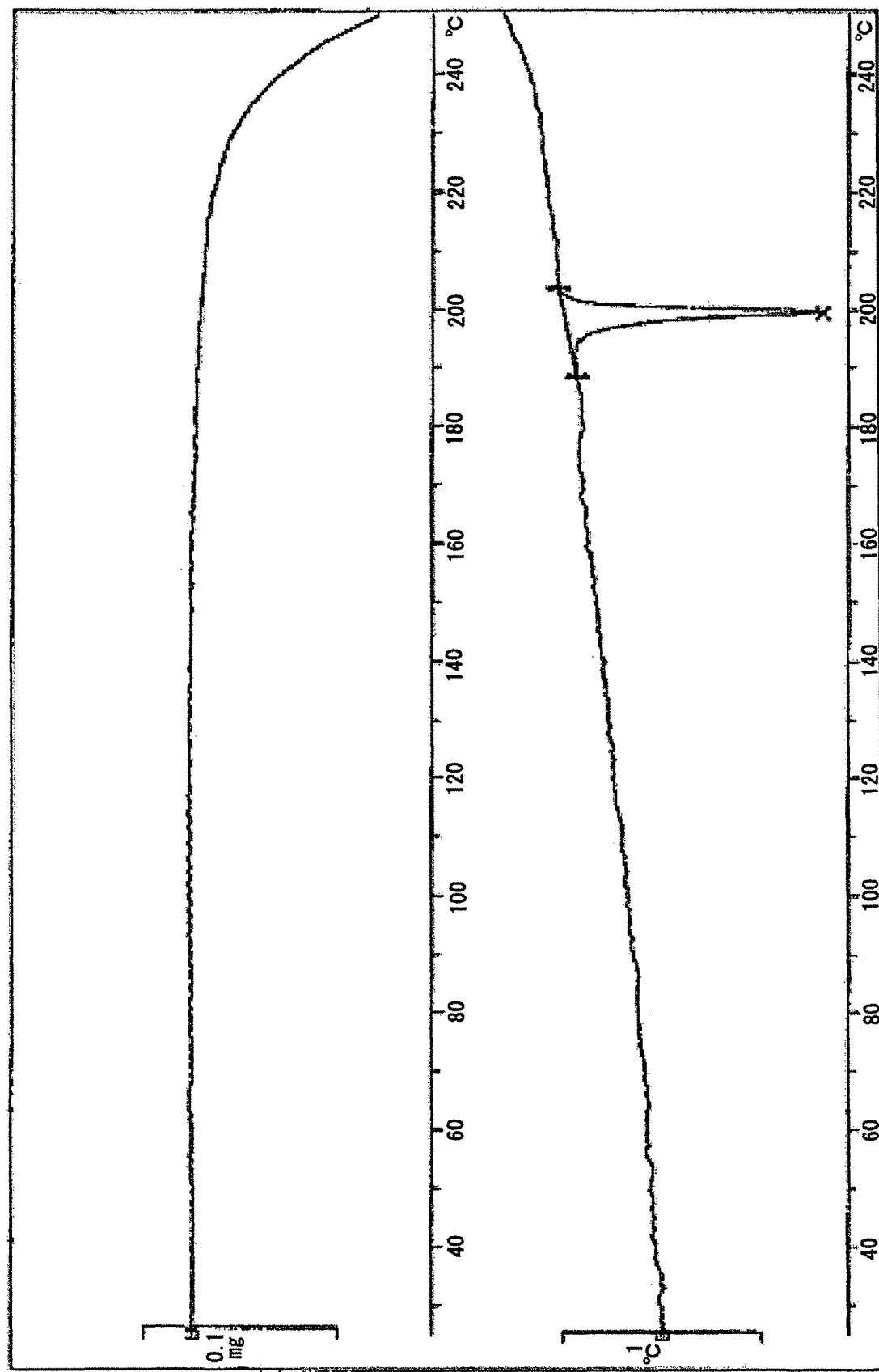

[Fig. 10]
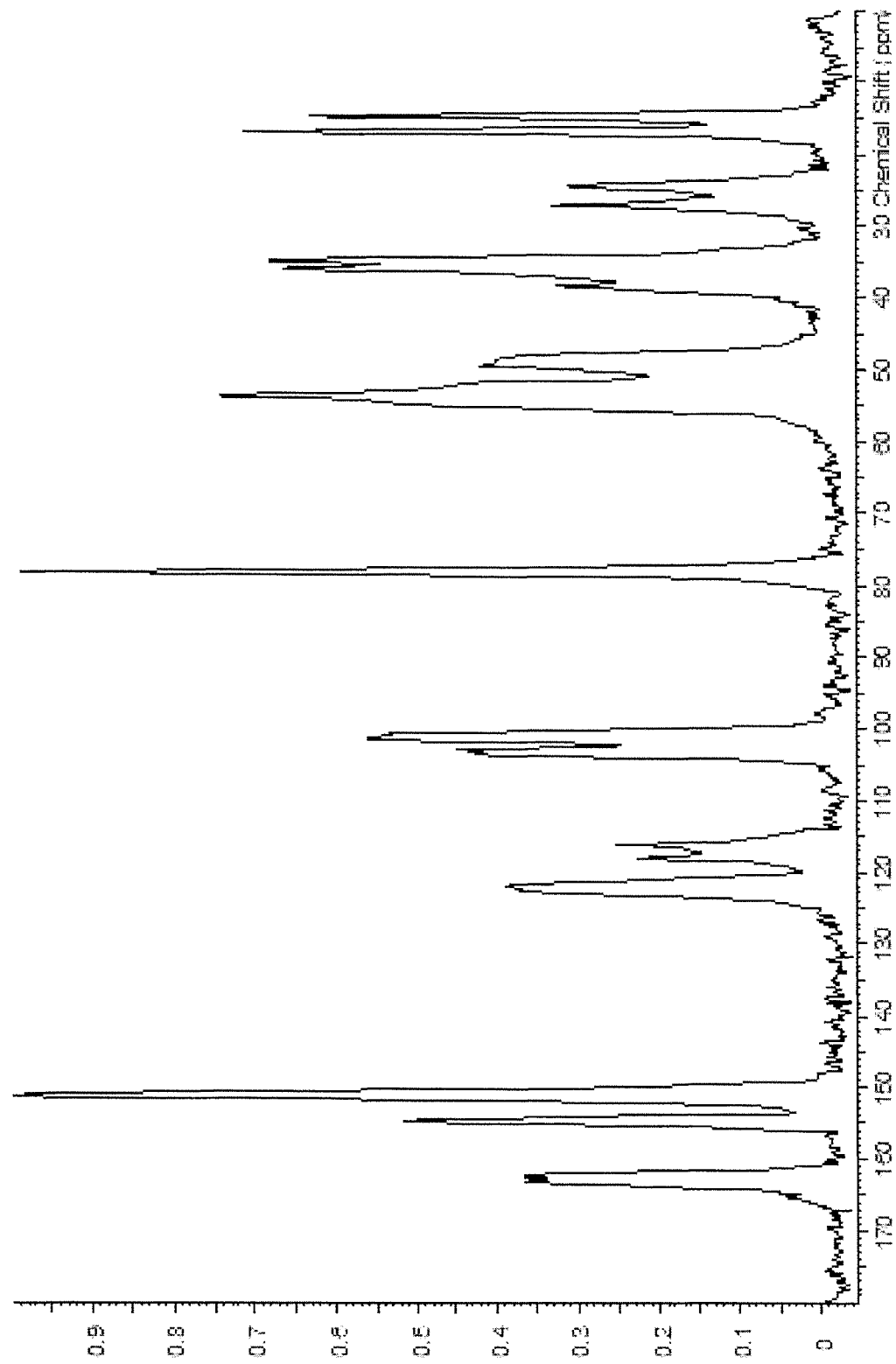

[Fig. 11]
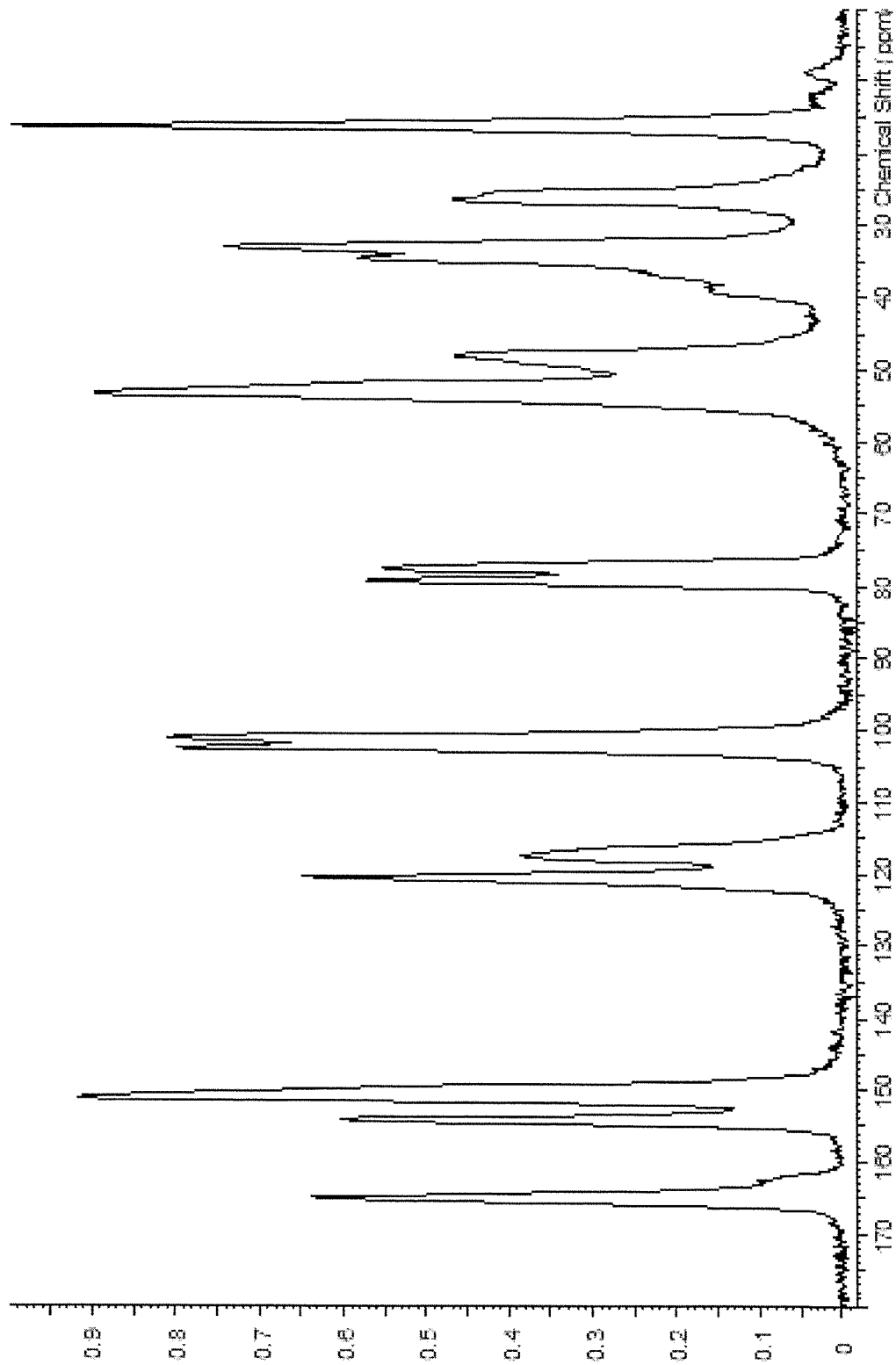

[Fig. 12]
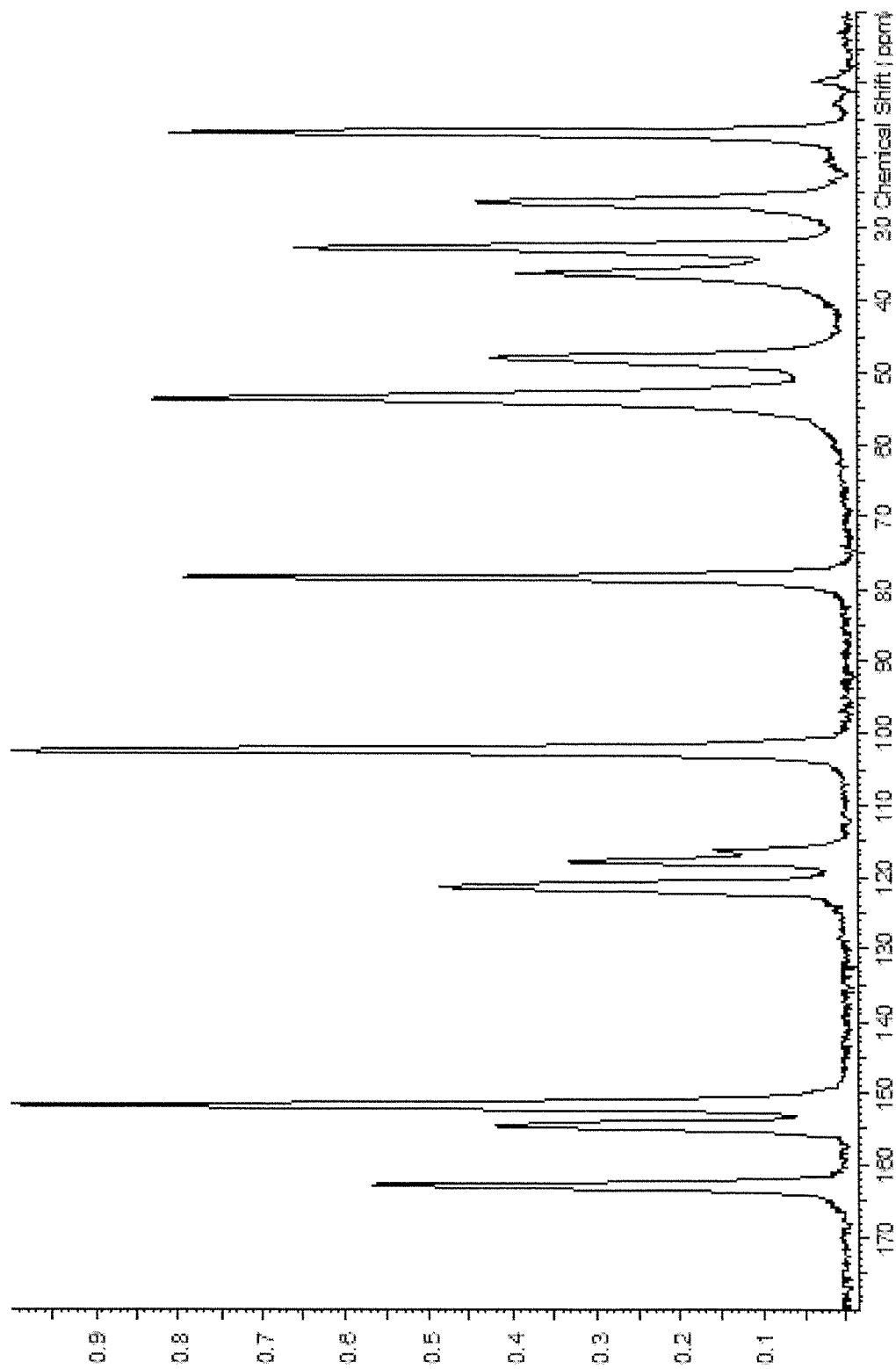

[Fig. 13]
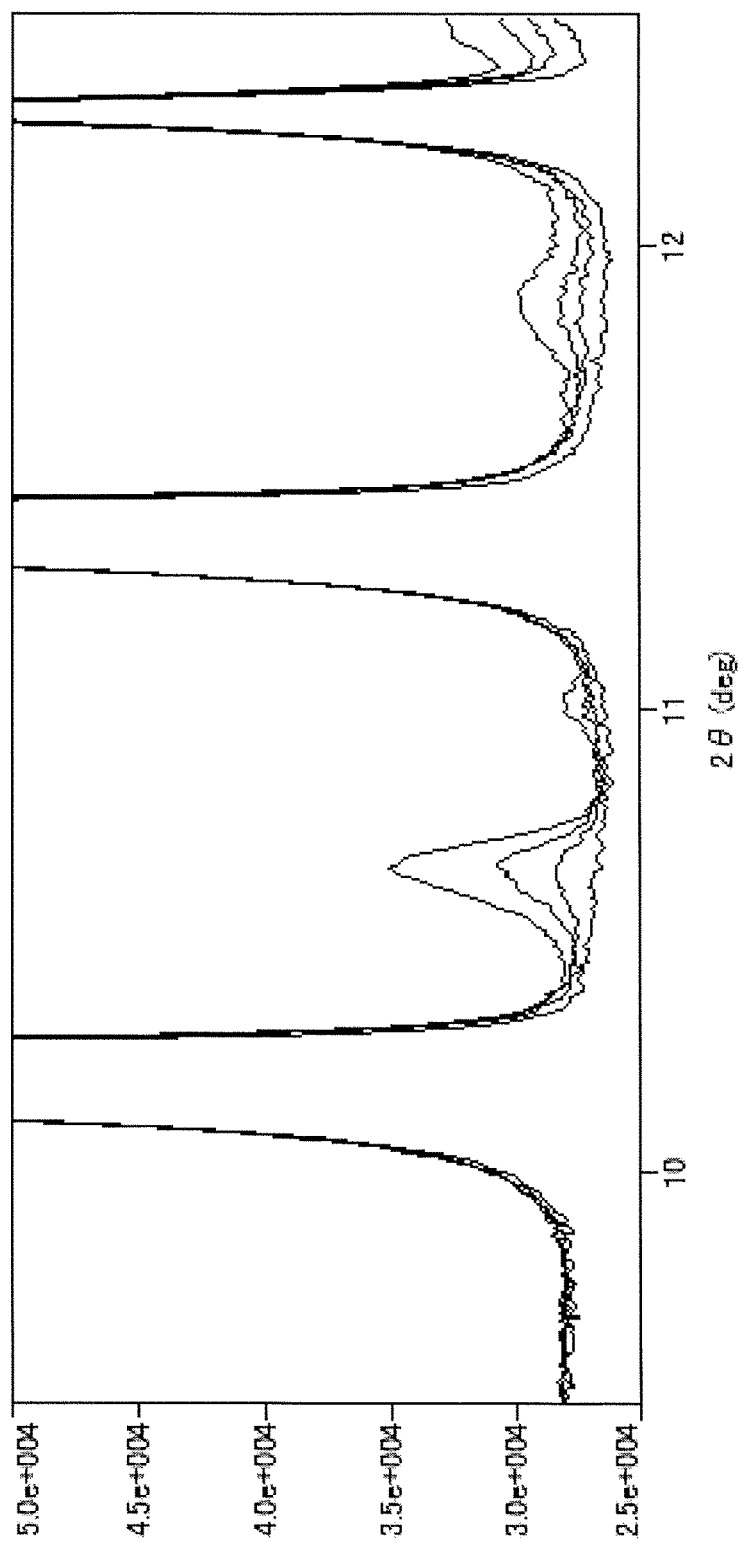

[Fig. 14]
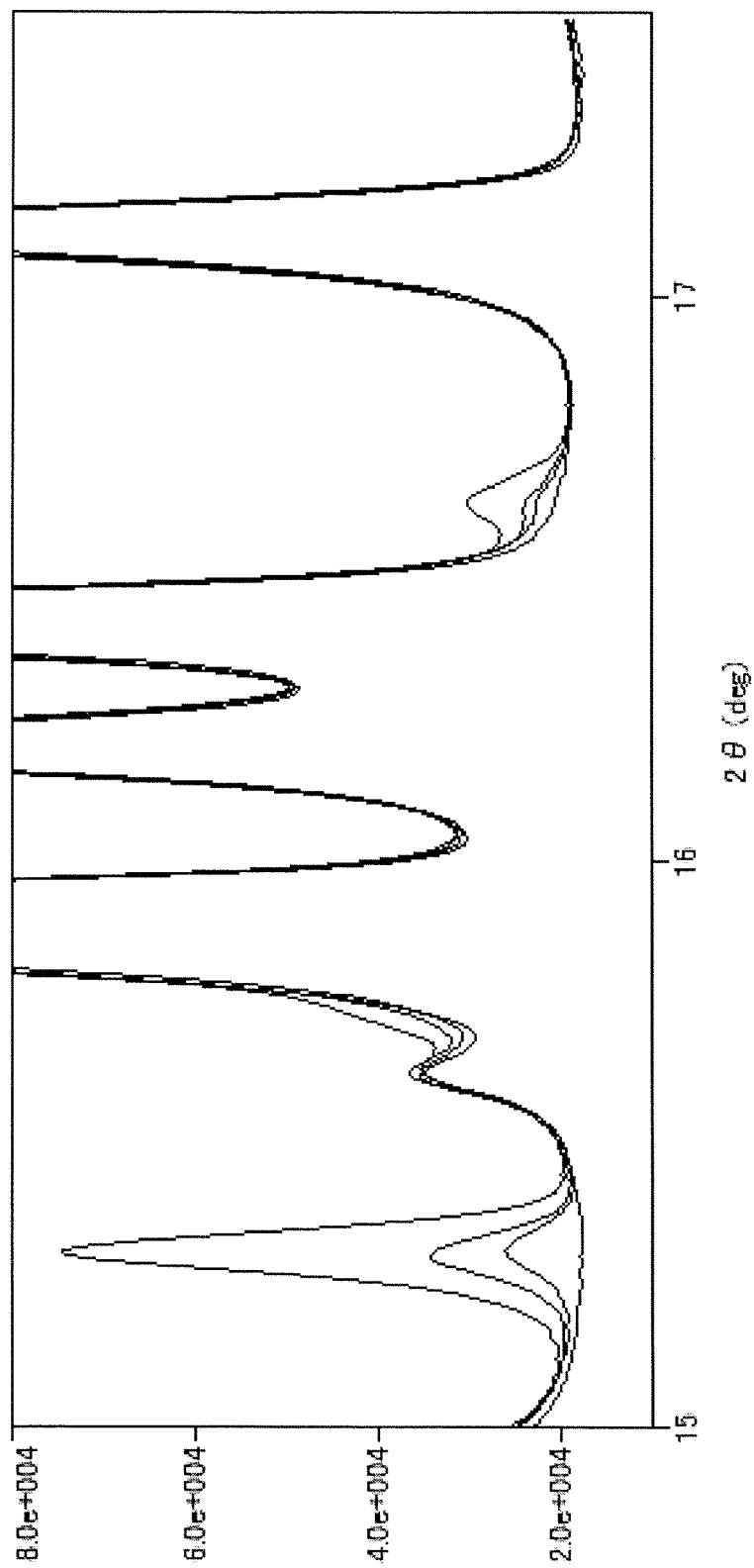

[Fig. 15]
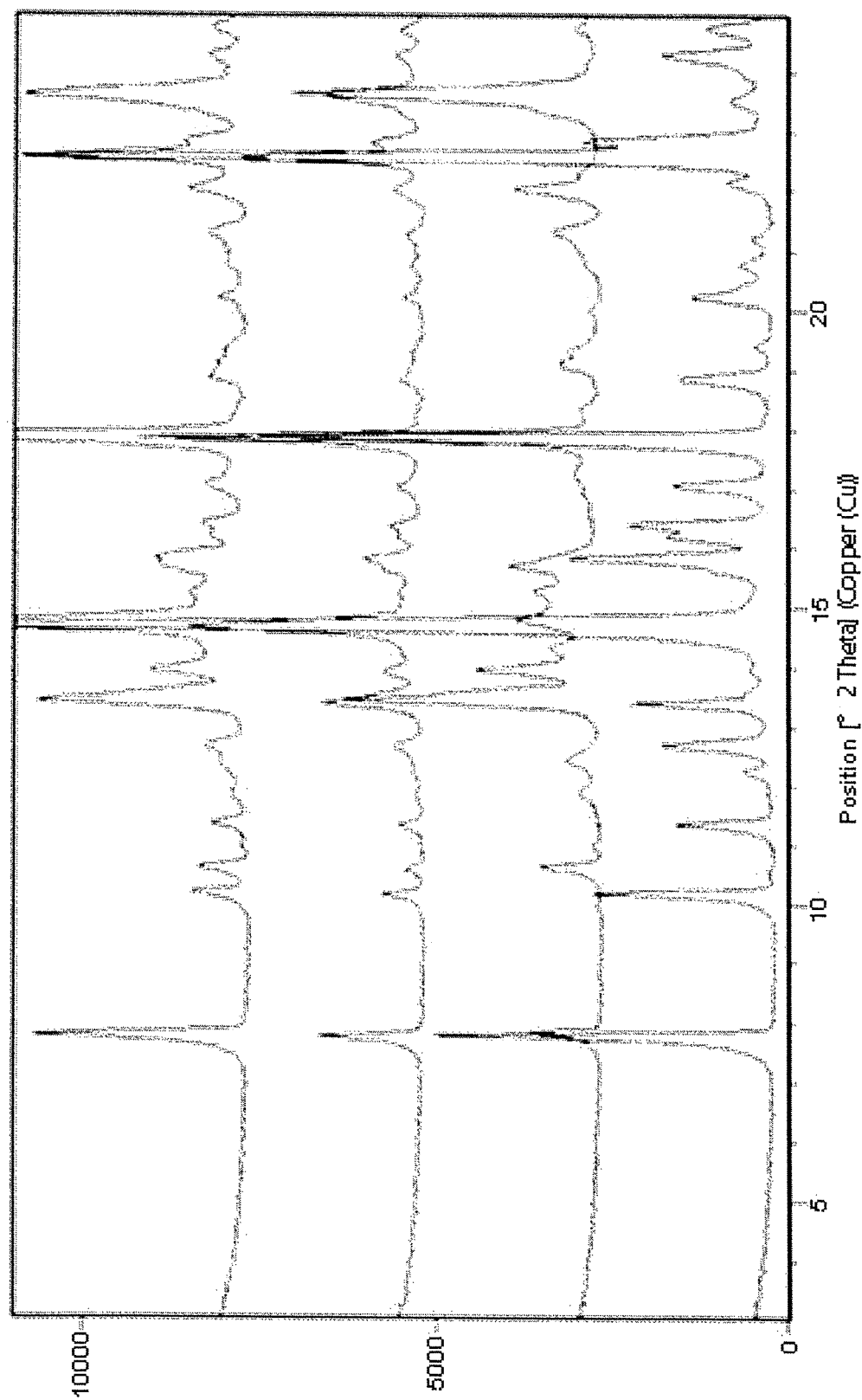

[Fig. 16]
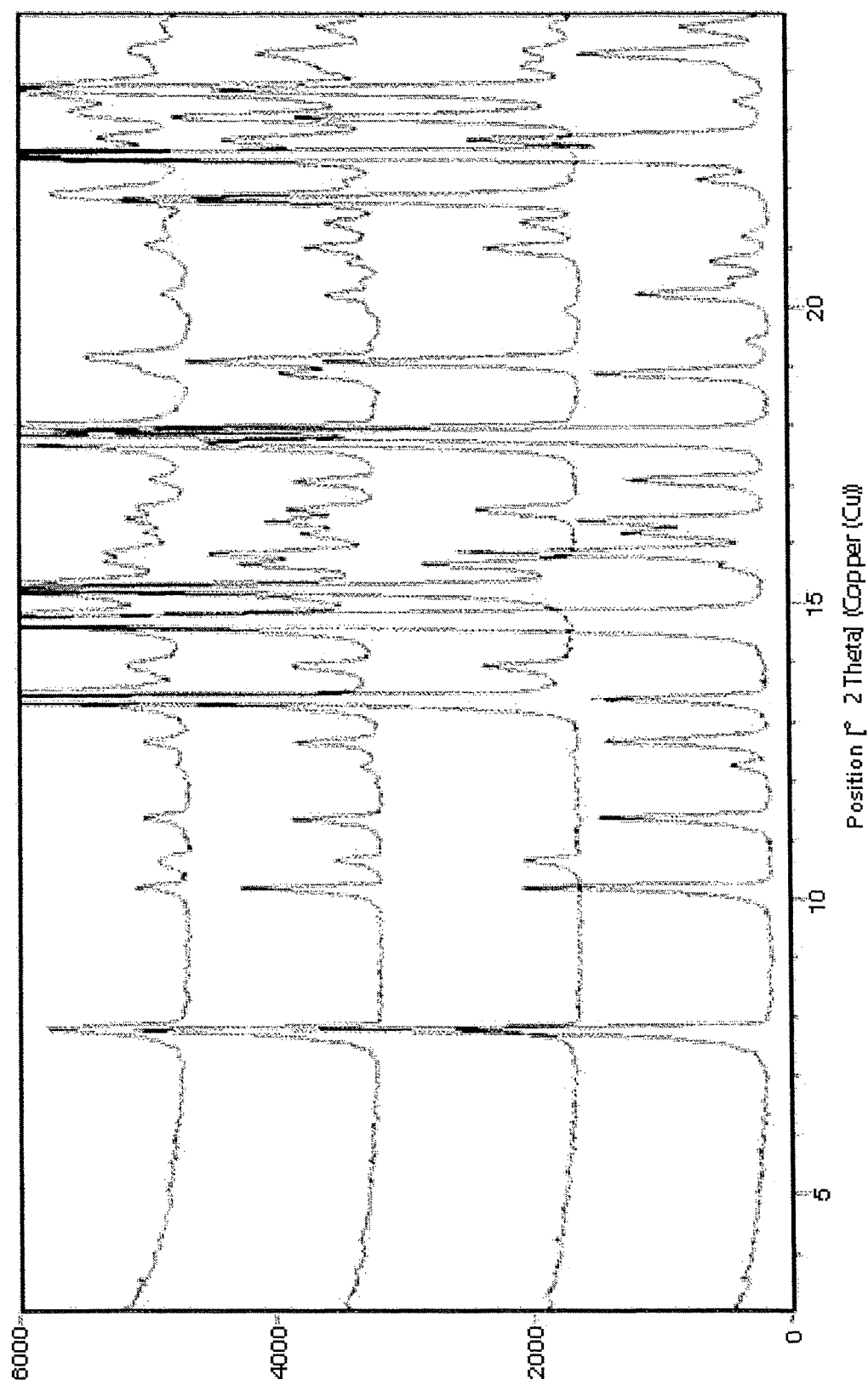

[Fig. 17]
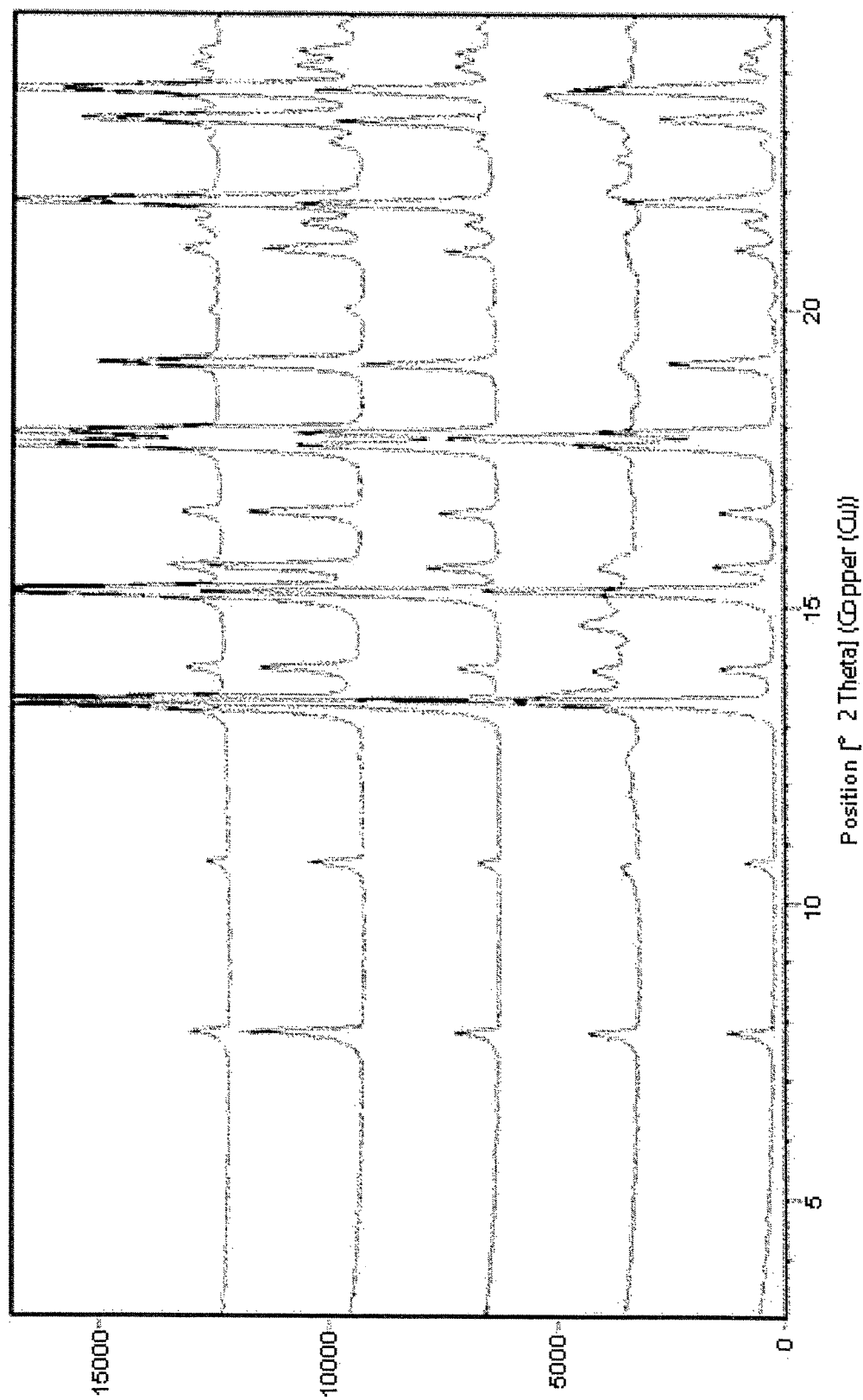

CRYSTALLINE FORMS OF A JANUS KINASE INHIBITOR

TECHNICAL FIELD

The present invention relates to crystalline forms of the Janus kinase (JAK) inhibitor 3-((3S,4R)-3-methyl-6-(7H-pyrrolo[2,3-d]pyrimidin-4-yl)-1,6-diazaspiro[3.4]octan-1-γ 1)-3-oxopropanenitrile (Compound A), as well as, compositions thereof, methods of their preparation, methods of use thereof, and methods of quantitation.

BACKGROUND ART

Janus kinase (JAK) inhibitors are of current interest for the treatment of various diseases including autoimmune diseases, inflammatory diseases, and cancer. To date, two JAK inhibitors have been approved by the U.S. Food & Drug Administration (FDA). Ruxolitinib has been approved for the treatment of primary myelofibrosis and polycythemia vera (PV), and tofacitinib has been approved for the treatment of rheumatoid arthritis. Other JAK inhibitors are in the literature. The compound 3-((3S,4R)-3-methyl-6-(7H-pyrrolo[2,3-d]pyrimidin-4-yl)-1,6-diazaspiro[3.4]octan-1-γ 1)-3-oxopropanenitrile (Compound A) (see structure below) is an example of a spirocyclic JAK inhibitor reported in U.S. Pat. Pub. Nos. 2011/0136778 and International Pat. Pub. No. PCT/JP2016/070046.

[Chem. 1]

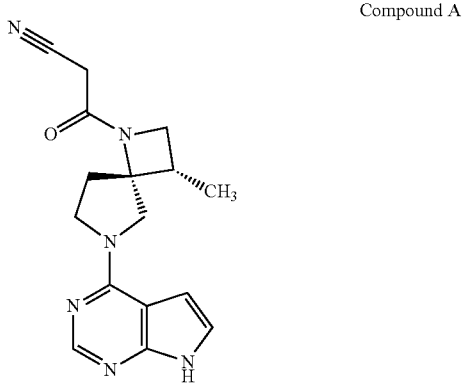

Compound A

Drug compounds like, for example, Compound A are typically combined with other pharmaceutically acceptable ingredients to form compositions suitable for administration to patients. Solid formulations often require that the drug compound have workable solid state characteristics such as stability to heat and humidity, ease of handling, and other characteristics that facilitate preparation of solid dosage forms. Accordingly, there is an ongoing need for solid forms of existing drug molecules. The crystalline forms of Compound A described herein are directed toward this end.

SUMMARY OF INVENTION

The present invention is directed to, inter alia, crystalline Forms β and γ of 3-((3S,4R)-3-methyl-6-(7H-pyrrolo[2,3-d]pyrimidin-4-yl)-1,6-diazaspiro[3.4]octan-1-γ 1)-3-oxopropanenitrile (Compound A).

The present invention is further directed to compositions comprising Form α together with Form β or Form γ or both.

The present invention is further directed to pharmaceutical compositions comprising one or more crystalline forms or compositions of the invention.

The present invention is further directed to methods of preparing the crystalline forms of the invention.

The present invention is further directed to methods of quantitating the crystalline forms of the invention.

The present invention is further directed to methods of inhibition of Janus kinase comprising contacting a crystalline form of the invention with a Janus kinase.

The present invention is further directed to a method of treating or preventing a disease in a patient comprising administering to a patient a therapeutically effective amount of a crystalline form or composition of the invention.

The present invention is further directed to a crystalline form or composition of the invention for use in prophylaxis or therapy.

The present invention is further directed to use of a crystalline form or composition of the invention for the preparation of a medicament for use in therapy or prophylaxis.

BRIEF DESCRIPTION OF DRAWINGS

FIG. 1 depicts an XRPD pattern consistent with Form α.
FIG. 2 depicts an XRPD pattern consistent with Form β.
FIG. 3 depicts an XRPD pattern consistent with Form γ.
FIG. 4 depicts a DSC thermogram consistent with Form α.
FIG. 5 depicts a DSC thermogram consistent with Form β.
FIG. 6 depicts a DSC thermogram consistent with Form γ.
FIG. 7 depicts TG-DTA data consistent with Form α.
FIG. 8 depicts TG-DTA data consistent with Form β.
FIG. 9 depicts TG-DTA data consistent with Form γ.
FIG. 10 depicts solid state $^{13}C$ NMR data consistent with Form α.
FIG. 11 depicts solid state $^{13}C$ NMR data consistent with Form β.
FIG. 12 depicts solid state $^{13}C$ NMR data consistent with Form γ.
FIG. 13 depicts overlayed XRPD patterns obtained from the standard sample of Compound A containing 0, 2, 5, and 10% Form β (See Example 4).
FIG. 14 depicts overlayed XRPD patterns obtained from the standard sample of Compound A containing 0, 1, 2, 5, and 10% Form γ (See Example 4).
FIG. 15 depicts XRPD patterns in Example 6 for Form α of Compound A used, Form β of Compound A used, the 1:1-by-weight mixture of Forms α and β of Compound A before stirring, and the crystal obtained after stirring, from the bottom.
FIG. 16 depicts XRPD patterns in Example 7 for Form α of Compound A used, Form γ of Compound A used, the 1:1-by-weight mixture of Forms α and γ of Compound A before stirring, and the crystal obtained after stirring, from the bottom.
FIG. 17 depicts XRPD patterns in Example 8 for Form γ of Compound A used, Form β of Compound A used, the 1:1-by-weight mixture of Forms β and γ of Compound A before stirring, the crystal obtained from formamide, that from N,N-dimethylformamide, and that from dimethylsulfoxide, from the bottom.

DESCRIPTION OF EMBODIMENTS

The present invention provides, inter alia, crystalline forms of 3-((3S,4R)-3-methyl-6-(7H-pyrrolo[2,3-d]pyrimidin-4-yl)-1,6-diazaspiro[3.4]octan-1-γ 1)-3-oxopropanenitrile which is an inhibitor of Janus kinase (JAK) and is useful in the treatment of various diseases associated with Janus kinase upregulation or overexpression. In some embodiments, the crystalline forms of the invention inhibit JAK3. In some embodiments, the crystalline forms of the invention inhibit JAK2.

One aspect of the present invention is as follows.

[Item 1] A crystalline form of 3-((3S,4R)-3-methyl-6-(7H-pyrrolo[2,3-d]pyrimidin-4-yl)-1,6-diazaspiro[3.4]octan-1-γ 1)-3-oxopropanenitrile having Form 3.

[Item 2] The crystalline form of Item 1, having an X-ray powder diffraction pattern comprising a characteristic peak, in terms of 2θ (°), at about 11.8.

[Item 3] The crystalline form of Item 1, having an X-ray powder diffraction pattern comprising two or more characteristic peaks, in terms of 2θ (°), selected from about 10.5, about 11.8, about 19.3, and about 22.0.

[Item 4] The crystalline form of Item 1, having an X-ray powder diffraction pattern comprising three or more characteristic peaks, in terms of 2θ (°), selected from about 7.8, about 10.5, about 11.8, about 13.4, about 13.9, about 17.8, about 19.3, about 22.0, about 23.6, and about 28.0.

[Item 5] The crystalline form of any one of Items 1 to 4, having a DSC thermogram which is characterized by an endothermic peak at about 186° C.

[Item 6] The crystalline form of any one of Items 1 to 5, having a solid state $^{13}C$ NMR spectrum which is characterized by at least one peak at about 165.1 ppm.

[Item 7] The crystalline form of any one of Items 1 to 5, having a solid state $^{13}C$ NMR spectrum which is characterized by at least 5 peaks selected from about 16.5, about 25.8, about 26.5, about 33.1, about 34.8, about 36.7, about 38.8, about 48.2, about 53.4, about 77.7, about 79.5, about 101.2, about 102.6, about 117.5, about 120.6, about 151.1, about 154.3, and about 165.1 ppm.

[Item 8] The crystalline form of any one of Items 1 to 7, having space group P1 with unit cell parameters:

TABLE 1

| a (Å) | 8.043 |
|---|---|
| b (Å) | 11.371 |
| c (Å) | 16.522 |
| α (°) | 97.537 |
| β (°) | 94.541 |
| γ (°) | 90.294. |

[Item 9] The crystalline form of any one of Items 1 to 8, having a purity of at least about 50%.

[Item 10] The crystalline form of any one of Items 1 to 8, having a purity of at least about 75%.

[Item 11] The crystalline form of any one of Items 1 to 8, having a purity of at least about 85%.

[Item 12] The crystalline form of any one of Items 1 to 8, having a purity of at least about 90%.

[Item 13] The crystalline form of any one of Items 1 to 8, having a purity of at least about 95%.

[Item 14] A crystalline form of 3-((3S,4R)-3-methyl-6-(7H-pyrrolo[2,3-d]pyrimidin-4-yl)-1,6-diazaspiro[3.4]octan-1-γ 1)-3-oxopropanenitrile having Form γ.

[Item 15] The crystalline form of Item 14, having an X-ray powder diffraction pattern comprising a characteristic peak, in terms of 2θ (0), at about 16.5.

[Item 16] The crystalline form of Item 14, having an X-ray powder diffraction pattern comprising two or more characteristic peaks, in terms of 2θ (°), selected from about 16.5, about 17.7, about 21.4, about 21.8, and about 23.1.

[Item 17] The crystalline form of Item 14, having an X-ray powder diffraction pattern comprising three or more characteristic peaks, in terms of 2θ (°), selected from about 7.7, about 10.6, about 13.3, about 13.9, about 15.5, about 16.5, about 17.7, about 17.9, about 19.0, about 21.4, about 21.8, and about 23.1, about 23.7, and about 28.1.

[Item 18] The crystalline form of any one of Items 14 to 17, having a DSC thermogram which is characterized by an endothermic peak at about 196° C.

[Item 19] The crystalline form of any one of Items 14 to 18, having a solid state $^{13}C$ NMR spectrum which is characterized by at least one peak at about 162.9 ppm.

[Item 20] The crystalline form of any one of Items 14 to 19, having a solid state $^{13}C$ NMR spectrum which is characterized by at least 5 peaks selected from about 16.9, about 26.5, about 32.9, about 36.4, about 48.1, about 53.7, about 78.6, about 102.6, about 116.4, about 117.9, about 121.5, about 151.8, about 154.6, and about 162.9 ppm.

[Item 21] The crystalline form of any one of Items 14 to 20, having space group P2₁ with unit cell parameters:

TABLE 2

| a (Å) | 8.095 |
|---|---|
| b (Å) | 8.017 |
| c (Å) | 11.459 |
| α (°) | 90 |
| β (°) | 95.663 |
| γ (°) | 90. |

[Item 22] The crystalline form of any one of Items 14 to 21, having a purity of at least about 50%.

[Item 23] The crystalline form of any one of Items 14 to 21, having a purity of at least about 75%.

[Item 24] The crystalline form of any one of Items 14 to 21, having a purity of at least about 85%.

[Item 25] The crystalline form of any one of Items 14 to 21, having a purity of at least about 90%.

[Item 26] The crystalline form of any one of Items 14 to 21, having a purity of at least about 95%.

[Item 27] A method of preparing the crystalline form of any one of Items 1 to 13, comprising crystallizing 3-((3S,4R)-3-methyl-6-(7H-pyrrolo[2,3-d]pyrimidin-4-yl)-1,6-diazaspiro[3.4]octan-1-γ 1)-3-oxopropanenitrile from solvent.

[Item 28] The method of Item 27 wherein the solvent comprises 1-butanol and acetonitrile.

[Item 29] The method of Item 28 wherein the ratio of 1-butanol to acetonitrile is about 1:3 (v/v).

[Item 30] Crystalline Form β prepared by the method of any one of Items 27 to 29.

[Item 31] A method of preparing the crystalline form of any one of Items 14 to 26, comprising converting 3-((3S,4R)-3-methyl-6-(7H-pyrrolo[2,3-d]pyrimidin-4-yl)-1,6-diazaspiro[3.4]octan-1-γ 1)-3-oxopropanenitrile, Form α, into Form γ.

[Item 32] A method of Item 31, comprising stirring 3-((3S,4R)-3-methyl-6-(7H-pyrrolo[2,3-d]pyrimidin-4-yl)-1,6-diazaspiro[3.4]octan-1-γ 1)-3-oxopropanenitrile, Form α, in dimethylformamide (DMF).

[Item 33] A method of Item 31, comprising stirring 3-((3S,4R)-3-methyl-6-(7H-pyrrolo[2,3-d]pyrimidin-4-yl)-1,6-diazaspiro[3.4]octan-1-γ 1)-3-oxopropanenitrile, Form α, in formamide.

[Item 34] Crystalline Form γ prepared by the method of any one of Items 31 to 33.

[Item 35] A composition of crystalline 3-((3S,4R)-3-methyl-6-(7H-pyrrolo[2,3-d]pyrimidin-4-yl)-1,6-diazaspiro[3.4]octan-1-γ 1)-3-oxopropanenitrile comprising Form α and Form β.

[Item 36] The composition of Item 35 consisting essentially of Form α and Form f.

[Item 37] The composition of Item 35 or 36, wherein Form β is present in an amount of about 1 to about 50% w/w with respect to Form α.

[Item 38] The composition of Item 35 or 36, wherein Form β is present in an amount of about 1 to about 20% w/w with respect to Form α.

[Item 39] The composition of Item 35 or 36, wherein Form β is present in an amount of about 1 to about 10% w/w with respect to Form α.

[Item 40] The composition of Item 35 or 36, wherein Form β is present in an amount of about 1 to about 5% w/w with respect to Form α.

[Item 41] The composition of any one of Items 35 to 40 further comprising Form γ.

[Item 42] A composition of crystalline 3-((3S,4R)-3-methyl-6-(7H-pyrrolo[2,3-d]pyrimidin-4-yl)-1,6-diazaspiro[3.4]octan-1-γ 1)-3-oxopropanenitrile comprising Form β and Form γ.

[Item 43] The composition of Item 42 consisting essentially of Form β and Form γ.

[Item 44] The composition of Item 42 or 43, wherein Form γ is present in an amount of about 1 to about 50% w/w with respect to Form β.

[Item 45] The composition of Item 42 or 43, wherein Form γ is present in an amount of about 1 to about 20% w/w with respect to Form 3.

[Item 46] The composition of Item 42 or 43, wherein Form γ is present in an amount of about 1 to about 10% w/w with respect to Form 3.

[Item 47] The composition of Item 42 or 43, wherein Form γ is present in an amount of about 1 to about 5% w/w with respect to Form 3.

[Item 48] The composition of any one of Items 42 to 47 further comprising Form α.

[Item 49] A pharmaceutical composition comprising the crystalline form or composition of any one of Items 1 to 48, and a pharmaceutically acceptable carrier.

[Item 50] The pharmaceutical composition of Item 49 further comprising a second therapeutic agent.

[Item 51] The pharmaceutical composition of Item 49 or 50 which is suitable for oral, parenteral, pulmonary, local, or topical administration.

[Item 52] The pharmaceutical composition of Item 49 or 50 which is suitable for topical administration.

[Item 53] The pharmaceutical composition of Item 49 or 50 in the form of a tablet, capsule, pill, powder, or ointment.

[Item 54] The pharmaceutical composition of Item 49 or 50 in the form of a powder suitable for reconstitution in liquid for IV, IM, or SC administration.

[Item 55] The pharmaceutical composition of Item 49 or 50, comprising white soft paraffin, hard paraffin, squalene, or a mixture thereof.

[Item 56] A method for inhibiting Janus kinase, comprising contacting the Janus kinase with a crystalline form or composition of any one of Items 1 to 55.

[Item 57] The method of Item 56, wherein the Janus kinase is Janus kinase 3 (JAK3).

[Item 58] The method of Item 56, wherein the Janus kinase is Janus kinase 2 (JAK2).

[Item 59] A method for treating or preventing a disease selected from organ transplant rejection, graft versus host reaction after transplantation, autoimmune disease, allergic diseases, and chronic myeloproliferative disease, comprising administering to a mammal a therapeutically effective amount of the crystalline form or composition of any one of Items 1 to 55.

[Item 60] A method for treating or preventing rheumatoid arthritis, psoriasis, alopecia areata, dry eye, atopic dermatitis, eczema, or hand eczema comprising administering to a mammal a therapeutically effective amount of the crystalline form or composition of any one of Items 1 to 55.

[Item 61] The crystalline form or composition of any one of Items 1 to 55 for use as a pharmaceutically active ingredient.

[Item 62] The crystalline form or composition of any one of Items 1 to 55 for use in the treatment or prevention of organ transplant rejection, graft versus host reaction after transplantation, autoimmune disease, allergic diseases, or chronic myeloproliferative disease.

[Item 63] The crystalline form of any one of Items 1 to 55 for use in the treatment or prevention of rheumatoid arthritis, psoriasis, alopecia areata, dry eye, atopic dermatitis, eczema, or hand eczema.

[Item 64] A method of measuring the amount of Form β present in a preparation of 3-((3S,4R)-3-methyl-6-(7H-pyrrolo[2,3-d]pyrimidin-4-yl)-1,6-diazaspiro[3.4]octan-1-γ 1)-3-oxopropanenitrile, Form α, comprising measuring the peak area of an XRPD peak that is characteristic of Form β, and comparing the peak area to a standard.

[Item 65] The method of Item 64 wherein the peak characteristic of Form β occurs at about 10.6° 2-theta.

[Item 66] A method of measuring the amount of Form γ present in a preparation of 3-((3S,4R)-3-methyl-6-(7H-pyrrolo[2,3-d]pyrimidin-4-yl)-1,6-diazaspiro[3.4]octan-1-γ 1)-3-oxopropanenitrile, Form α, comprising measuring the peak area of an XRPD peak that is characteristic of Form γ, and comparing the peak area to a standard.

[Item 67] The method of Item 66 wherein the peak characteristic of Form γ occurs at about 16.6° 2-theta.

As used herein, "crystalline form" is meant to refer to a certain lattice configuration of a crystalline substance. Different crystalline forms of the same substance typically have different crystalline lattices (e.g., unit cells) and different physical properties attributed to their different crystalline lattices, and in some instances, have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), solid state NMR and the like further help identify the crystalline form as well as help determine stability and solvent/water content.

Different crystalline forms of a particular substance can include both anhydrous forms of that substance and solvated/hydrated forms of that substance, where each of the anhydrous forms and solvated/hydrated forms are distinguished from each other by different XRPD patterns, thereby signifying different crystalline lattices. In some instances, a single crystalline form (e.g., identified by a unique XRPD pattern) can have variable water or solvent content, where the lattice remains substantially unchanged (as does the XRPD pattern) despite the compositional variation with respect to water and/or solvent.

An XRPD pattern of reflections (peaks) is typically considered a fingerprint of a particular crystalline form. It is well known that the relative intensities of the XRPD peaks can vary depending on, inter alia, the sample preparation technique, crystal size distribution, the sample mounting procedure, and the particular instrument employed. In some instances, new peaks may be observed or existing peaks may disappear, depending on the type of the machine or the settings (for example, whether a Ni filter is used or not). Moreover, instrument variation and other factors can affect the 2-theta values. Thus, peak assignments, such as those reported herein, can vary by ±0.2°, ±0.1° or ±0.04° (2-theta), and the term "substantially" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Thus, temperature values, such as those reported herein, can vary by ±3° C., and a crystalline form reported herein having a DSC thermogram or other thermogram "substantially" as shown in any of the Figures is understood to accommodate such variation.

Additionally, chemical shifts can vary by ±0.2 ppm in $^{13}$C NMR spectra, and the term "substantially" as used in the context of NMR data herein is meant to encompass this variation.

Form β

The present invention provides a crystalline form of 3-((3S,4R)-3-methyl-6-(7H-pyrrolo[2,3-d]pyrimidin-4-yl)-1,6-diazaspiro[3.4]octan-1-γ 1)-3-oxopropanenitrile (Compound A) having Form β. The crystalline form corresponding to Form β is believed to be anhydrous as evidenced by, for example, DSC and TG-DTA (see Example 2). In some embodiments, Form β has an X-ray powder diffraction pattern comprising a characteristic peak, in terms of 2θ (°), at about 11.8. In further embodiments, Form β has an X-ray powder diffraction pattern comprising two or more characteristic peaks, in terms of 2θ (°), selected from about 10.5, about 11.8, about 19.3, and about 22.0. In yet further embodiments, Form β has an X-ray powder diffraction pattern comprising three or more characteristic peaks, in terms of 2θ (°), selected from about 7.8, about 10.5, about 11.8, about 13.4, about 13.9, about 17.8, about 19.3, about 22.0, about 23.6, and about 28.0. In yet further embodiments, Form β has an X-ray powder diffraction pattern comprising three or more characteristic peaks, in terms of 2θ (°), selected from any of the peaks listed in Table 2-1 (see Example 2). In yet further embodiments, Form β has an XRPD pattern substantially as shown in FIG. 2.

In some embodiments, Form β has a DSC thermogram which is characterized by an endothermic peak at about 186° C. In some embodiments, Form β has a DSC thermogram which is characterized by an extrapolated onset temperature at about 185° C. In yet further embodiments, Form β has a DSC thermogram substantially as shown in FIG. 5.

In some embodiments, Form β has a solid state $^{13}$C NMR spectrum which is characterized by at least one peak at about 165.1 ppm. In further embodiments, Form β has a solid state $^{13}$C NMR spectrum which is characterized by at least 5 peaks selected from about 16.5, about 25.8, about 26.5, about 33.1, about 34.8, about 36.7, about 38.8, about 48.2, about 53.4, about 77.7, about 79.5, about 101.2, about 102.6, about 117.5, about 120.6, about 151.1, about 154.3, and about 165.1 ppm. In yet further embodiments, Form β has a $^{13}$C NMR spectrum substantially as shown in FIG. 11.

In some embodiments, Form β has space group P1 with unit cell parameters:

TABLE 3

| | |
|---|---|
| a (Å) | 8.043 |
| b (Å) | 11.371 |
| c (Å) | 16.522 |

TABLE 3-continued

| | |
|---|---|
| α (°) | 97.537 |
| β (°) | 94.541 |
| γ (°) | 90.294 | as determined by single crystal X-ray diffraction (see Example 5).

Form β can have a purity level of at least about 50%, at least about 75%, at least about 85%, at least about 90%, or at least about 95%. In some embodiments, Form β is substantially pure.

Form β can be prepared by crystallizing 3-((3S,4R)-3-methyl-6-(7H-pyrrolo[2,3-d]pyrimidin-4-yl)-1,6-diazaspiro[3.4]octan-1-γ 1)-3-oxopropanenitrile (Compound A) from solvent. For example, Compound A (e.g., as Form α) can be combined with solvent to form α solution or slurry, from which crystals of Form β are obtained. In some embodiments, the solvent includes a nitrile such as acetonitrile or a mixture of 1-butanol and acetonitrile. In some embodiments, the solvent comprises about 1:3 (v/v) of 1-butanol and acetonitrile, respectively. In some embodiments, Compound A can be combined with solvent and heated to a temperature between about 30 and about 50° C. In some embodiments, the mixture can be heated to between about 35 and about 45° C., or to about 40° C. After heating, the mixture can be cooled, such as to about room temperature (e.g., about 23° C.), to provide Form β crystalline product.

The present invention further provides Form β prepared by any one of the methods described above.

Form γ

The present invention also provides a crystalline form of 3-((3S,4R)-3-methyl-6-(7H-pyrrolo[2,3-d]pyrimidin-4-yl)-1,6-diazaspiro[3.4]octan-1-γ 1)-3-oxopropanenitrile (Compound A) having Form γ. The crystalline form corresponding to Form γ is believed to be anhydrous as evidenced by, for example, DSC and TG-DTA (see Example 3). In some embodiments, Form γ has an X-ray powder diffraction pattern comprising a characteristic peak, in terms of 2θ (°), at about 16.5. In further embodiments, Form γ has an X-ray powder diffraction pattern comprising two or more characteristic peaks, in terms of 2θ (°), selected from about 16.5, about 17.7, about 21.4, about 21.8, and about 23.1. In yet further embodiments, Form γ has an X-ray powder diffraction pattern comprising three or more characteristic peaks, in terms of 2θ (°), selected from about 7.7, about 10.6, about 13.3, about 13.9, about 15.2, about 16.5, about 17.7, about 17.9, about 19.0, about 21.4, about 21.8, and about 23.1, about 23.7, and about 28.1. In yet further embodiments, Form γ has an X-ray powder diffraction pattern comprising three or more characteristic peaks, in terms of 2θ (°), selected from any of the peaks listed in Table 3-1 (see Example 3). In yet further embodiments, Form γ has an XRPD pattern substantially as shown in FIG. 3.

In some embodiments, Form γ has a DSC thermogram which is characterized by an endothermic peak at about 196° C. In some embodiments, Form γ has a DSC thermogram which is characterized by an extrapolated onset temperature at about 196° C. In yet further embodiments, Form γ has a DSC thermogram substantially as shown in FIG. 6.

In some embodiments, Form γ has a solid state $^{13}$C NMR spectrum which is characterized by at least one peak at about 162.9 ppm. In further embodiments, Form γ has a solid state $^{13}$C NMR spectrum which is characterized by at least 5 peaks selected from about 16.9, about 26.5, about 32.9, about 36.4, about 48.1, about 53.7, about 78.6, about 102.6, about 116.4, about 117.9, about 121.5, about 151.8, about 154.6, and about 162.9 ppm. In yet further embodiments, Form γ has a $^{13}$C NMR spectrum substantially as shown in FIG. 11.

In some embodiments, Form γ has space group P2$_1$ with unit cell parameters:

TABLE 4

| | |
|---|---|
| a (Å) | 8.095 |
| b (Å) | 8.017 |
| c (Å) | 11.459 |
| α (°) | 90 |
| β (°) | 95.663 |
| γ (°) | 90 | as determined by single crystal X-ray diffraction (see Example 5).

Form γ can have a purity level of at least about 50%, at least about 75%, at least about 85%, at least about 90%, or at least about 95%. In some embodiments, Form γ is substantially pure.

Form γ can be prepared by converting 3-((3S,4R)-3-methyl-6-(7H-pyrrolo[2,3-d]pyrimidin-4-yl)-1,6-diazaspiro[3.4]octan-1-γ 1)-3-oxopropanenitrile, Form α, into Form γ. The conversion can be carried out, for example, by stirring Form α in dimethylformamide (DMF). The stirring can be carried out at, for example, room temperature. Alternately, Form γ can be prepared by combining Compound A with formamide and adding Form γ seed crystal. The preparation can be carried out at room temperature and optionally under inert atmosphere such as nitrogen.

The present invention further provides Form γ prepared by any one of the methods described above.

Compositions

In addition to Forms β and γ, Compound A can be prepared and obtained as anhydrous crystalline Form α, which is described in Example 1. Accordingly, the present invention provides mixtures of two or more of Forms α, β, and γ of Compound A.

In some embodiments, the present invention provides a composition of crystalline 3-((3S,4R)-3-methyl-6-(7H-pyrrolo[2,3-d]pyrimidin-4-yl)-1,6-diazaspiro[3.4]octan-1-γ 1)-3-oxopropanenitrile (Compound A) comprising both Form α and Form β. In some embodiments, Form β is present in an amount of about 1 to about 50% w/w with respect to Form α. In further embodiments, Form β is present in an amount of about 1 to about 20% w/w with respect to Form α. In yet further embodiments, Form β is present in an amount of about 1 to about 10% w/w with respect to Form α. And in yet further embodiments, Form β is present in an amount of about 1 to about 5% w/w with respect to Form α. In some embodiments, the composition comprises Form α and Form β and is substantially free of other crystalline forms of Compound A. In further embodiments, the composition comprising Form α and Form β further comprises Form γ. In some embodiments, the composition consists essentially of Form α and Form 3.

Additionally, the present invention provides a composition of crystalline 3-((3S,4R)-3-methyl-6-(7H-pyrrolo[2,3-d]pyrimidin-4-yl)-1,6-diazaspiro[3.4]octan-1-γ 1)-3-oxopropanenitrile (Compound A) comprising both Form β and Form γ. In some embodiments, Form γ is present in an amount of about 1 to about 50% w/w with respect to Form β. In further embodiments, Form γ is present in an amount of about 1 to about 20% w/w with respect to Form β. In yet further embodiments, Form γ is present in an amount of about 1 to about 10% w/w with respect to Form β. And in yet further embodiments, Form γ is present in an amount of about 1 to about 5% w/w with respect to Form β. In some embodiments, the composition comprises Form β and Form γ and is substantially free of other crystalline forms of Compound A. In further embodiments, the composition comprising Form β and Form γ further comprises Form α. In some embodiments, the composition consists essentially of Form β and Form γ.

The present invention further provides compositions containing Form β or Form γ and one or more other substances. In some embodiments, the composition contains at least about 50%, at least about 70%, at least about 80%, at least about 90%, at least about 95%, at least about 97%, at least about 98%, or at least about 99%, by weight of Form β or Form γ.

Analytical Methods

The present invention provides a method of determining the amount of Form β present in a preparation of Form α comprising measuring the peak area of an XRPD peak that is characteristic of Form β, and comparing the peak area to a standard. In some embodiments, the peak characteristic of Form β occurs at about 10.6° 2-theta. The standard can be a standard curve calculated from peak areas of known amounts of Form β in Form α. Similarly, the present invention provides a method of measuring the amount of Form γ present in a preparation of Form α comprising measuring the peak area of an XRPD peak that is characteristic of Form γ, and comparing the peak area to a standard. In some embodiments, the peak characteristic of Form γ occurs at about 16.6° 2-theta. The standard can be a standard curve calculated from peak areas of known amounts of Form γ in Form α.

Pharmaceutical Compositions and Uses

The crystalline forms of the invention can be prepared as pharmaceutical compositions which comprise a crystalline form of the invention, or a composition of the invention, together with at least one pharmaceutically acceptable carrier (or excipient). In one embodiment, the pharmaceutical composition is suitable for oral, parenteral, pulmonary, local, or topical administration. In some embodiments, the pharmaceutical composition is in the form of an oral preparation such as tablet, capsule, granule, powder, lozenge, syrup, emulsion, suspension, or a parenteral preparation such as external preparation, suppository, injection, drop, nasal drug, pulmonary drug. In some embodiments, the pharmaceutical composition is suitable for topical application, such as an ointment.

The pharmaceutical compositions of the present invention may be prepared by mixing one or more crystalline forms of the invention, or a composition of the invention, with at least one or more pharmaceutically acceptable carriers in appropriate amounts according to known methods in the medicinal preparation field. The amount of Compound A in the pharmaceutical composition depends on its dosage forms, dosage amounts, etc., and can be, for example, about 0.1 to 100% by weight of the composition. The pharmaceutical compositions of the present invention can be, for example, in the form of a tablet, capsule, pill, powder, or ointment. In some embodiments, the pharmaceutical compositions of the present invention can be in the form of a powder suitable for reconstitution in liquid for intravenous (IV), intramuscular (IM), or subcutaneous (SC) administration. Additionally, the pharmaceutical compositions of the present invention may further comprise a second therapeutic agent.

The "pharmaceutically acceptable carrier" includes various conventional organic or inorganic carrier substances for pharmaceutical materials, e.g., a diluent, a disintegrant, a binder, a fluidizer, and a lubricant for solid preparations, a solvent, a solubilizing agent, a suspending agent, a tonicity agent, a buffer, and a soothing agent for liquid preparations, and a base, an emulsifier, a humectant, a stabilizer, a stabilizing agent, a dispersant, a plasticizer, a pH regulator, an absorption promoter, a gelling agent, an antiseptic, a filler, a resolvent, a solubilizing agent, and a suspending agent for semisolid preparations. Further, an additive including a preserving agent, an antioxidant agent, a colorant, and a sweetening agent may be used, if needed.

Examples of diluents include lactose, sucrose, D-mannitol, D-sorbitol, cornstarch, dextrin, microcrystalline cellulose, crystalline cellulose, carmellose, carmellose calcium, sodium carboxymethyl starch, low-substituted hydroxypropylcellulose, gum arabic, etc.

Examples of disintegrants include carmellose, carmellose calcium, carmellose sodium, sodium carboxymethyl starch, croscarmellose sodium, crospovidone, low-substituted hydroxypropylcellulose, hydroxypropylmethylcellulose, crystalline cellulose, etc.

Examples of binders include hydroxypropylcellulose, hydroxypropylmethylcellulose, povidone, crystalline cellulose, sucrose, dextrin, starch, gelatin, carmellose sodium, gum arabic, etc.

Examples of fluidizers include light anhydrous silicic acid, magnesium stearate, etc.

Examples of lubricants include magnesium stearate, calcium stearate, talc, etc.

Examples of a solvent medium include purified water, ethanol, propylene glycol, macrogol, sesame oil, corn oil, olive oil, etc.

Examples of a solubilizing agent include propylene glycol, D-mannitol, benzyl benzoate, ethanol, triethanolamine, sodium carbonate, sodium citrate, etc.

Examples of suspending agents include benzalkonium chloride, carmellose, hydroxypropylcellulose, propylene glycol, povidone, methylcellulose, glyceryl monostearate, etc.

Examples of tonicity agents include glucose, D-sorbitol, sodium chloride, D-mannitol, etc.

Examples of buffers include sodium hydrogen phosphate, sodium acetate, sodium carbonate, sodium citrate, etc.

Examples of soothing agents include benzyl alcohol, etc.

Examples of preserving agents include ethyl paraoxybenzoate, chlorobutanol, benzyl alcohol, sodium dehydroacetate, sorbic acid, etc.

Examples of antioxidant agents include sodium sulfite, ascorbic acid, etc.

Examples of colorants include food dye (e.g., Food Red No. 2 or 3, Food Yellow No. 4 or 5, etc.), n-carotene, etc.

Examples of sweetening agents include saccharin sodium, dipotassium glycyrrhizinate, aspartame, etc.

The pharmaceutical compositions of the present invention may be orally or parenterally (e.g., locally, rectally, intravenously, etc.) administered to a patient such as a non-human mammal (e.g., mice, rats, hamsters, guinea pigs, rabbits, cats, dogs, pigs, cows, horses, sheep, monkeys, etc.) or to human beings in a therapeutically effective amount for the treatment or prevention of disease. The term "mammal" is meant to include both human and non-human mammalian subjects. A dose of the pharmaceutical composition depends on the subjects, diseases, conditions, dosage forms, administration routes. The dose for orally administering to adult patients (body weight: about 60 kg) who are suffering from organ transplant rejection, graft versus host reaction after transplantation, autoimmune disease or allergic disease, etc. can be, for example, in the range from about 1 mg to 1 g per day. The dose may be administered at one time or in several divided doses.

For topical pharmaceutical compositions, the carrier (or diluent) can comprise white soft paraffin, hard paraffin, squalene, or a combination thereof. White soft paraffin, hard paraffin and squalane may be combined at a blend ratio of 70 to 90% by weight, 5 to 10% by weight and 5 to 20% by weight, respectively. An example preparation contains Compound A, white soft paraffin, 5±2% by weight of hard paraffin and 10±2% by weight of squalane.

A topical agent can be applied, for example, by application, inunction or spraying depending on the dosage form, etc. An application amount of the topical agent to the affected area can be selected depending on the content of the active ingredient, etc., and the topical agent can be applied, for example, at a time or in several divided amounts per day. In some embodiments, application is once daily or twice daily.

Pharmaceutical compositions can be prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985), which is incorporated herein by reference in its entirety.

The crystalline forms of the invention can be used in a method for inhibiting a Janus kinase, such as inhibiting JAK3, JAK2, or both, comprising contacting the crystalline form of the invention with the Janus kinase inhibitor. The contacting can occur in vitro or in vivo.

The crystalline forms or compositions of the invention may be used as the active ingredient in a method of treating or preventing one or more of the following diseases in a patient:

(a) organ transplant rejection, or graft versus host reaction after transplantation;

(b) autoimmune diseases including rheumatoid arthritis, psoriasis, psoriatic arthritis, multiple sclerosis, ulcerative colitis, Crohn's disease, systemic lupus erythematosus, type I diabetes, myasthenia gravis, Castleman's disease, juvenile idiopathic arthritis, dry eye; and (c) allergic diseases including asthma, atopic dermatitis, rhinitis.

In some embodiments, the crystalline forms of the invention may be used as the active ingredient of a therapeutic or preventive agent for rheumatoid arthritis, psoriasis, alopecia areata, dry eye, atopic dermatitis, eczema, or hand eczema.

The crystalline forms of the invention may be used as the active ingredient of a therapeutic or preventive agent for chronic myeloproliferative diseases including polycythemia vera, primary myelofibrosis, essential thrombocythemia, etc.

The term "therapeutically effective amount" of the compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject.

The term "treating" as used herein includes amelioration of a symptom, prevention of an aggravation, maintenance of a remission, prevention of an exacerbation, and prevention of a recurrence. The term "treating" may also include the delaying of the progression of the disease, disorder or condition, the amelioration, alleviation or relief of symptoms and complications, and/or cure or elimination of the disease, disorder or condition.

The term "treating" may also mean the management and care of a patient for the purpose of combating the disease, condition or disorder.

The term "preventing" refers to suppressing occurrence of a symptom.

Combination Therapy

The crystalline forms of the invention can be administered to a patient in combination with a therapeutically effective amount of one or more additional therapeutic agents. The crystalline form of the invention can be administered concurrently (e.g., together) with the additional therapeutic agent (e.g., in a single fixed-dosage form or in separate dosage forms). Similarly, the crystalline form of the invention and additional therapeutic agent can be administered to a patient sequentially. For example, the additional therapeutic agent is administered while the crystalline form of the invention exerts its therapeutic effect, or vice versa.

In order that the invention disclosed herein may be more efficiently understood, examples are provided below. It should be understood that these examples are for illustrative purposes only and are not to be construed as limiting the invention in any manner.

EXAMPLES

Example 1

Preparation of 3-((3S,4R)-3-methyl-6-(7H-pyrrolo [2,3-d]pyrimidin-4-yl)-1,6-diazaspiro[3.4]octan-1-γ 1)-3-oxopropanenitrile (Compound A) and Characterization of Crystalline Form α

Preparation of Compound A

Compound A was prepared by the synthetic method below as described in PCT/JP2016/070046 (Examples 1-15). In the crystallization steps, seed crystal was used to facilitate the crystallizations, but it is possible to prepare the crystals of each compound according to the processes described without seed crystal.

The abbreviations used herein have the meanings as follows:

S-BAPO: (S)-2-(benzylamino) propan-1-ol

S-BBMO: tert-butyl (S)—N-benzyl-N-(1-hydroxypropan-2-yl)glycinate

R-BCAB: tert-butyl (R)—N-benzyl-N-(2-chloropropyl) glycinate

S-MABB: tert-butyl (3S)-1-benzyl-3-methylazetidine-2-carboxylate

S-MABB-HC: tert-butyl (3S)-1-benzyl-3-methylazetidine-2-carboxylate hydrochloride S-MACB-HC: tert-butyl (3S)-3-methylazetidine-2-carboxylate hydrochloride S-ZMAB: 1-benzyl 2-(tert-butyl) (3S)-3-methylazetidine-1,2-dicarboxylate RS-ZMBB: 1-benzyl 2-(tert-butyl) (2R,3S)-2-(2-(tert-butoxy)-2-oxoethyl)-3-methylazetidine-1,2-dicarboxylate RS-ZMAA: (2R,3S)-1-((benzyloxy)carbonyl)-2-(carboxymethyl)-3-methylazetidine-2-carboxylic acid RS-ZMAA-DN.2H$_2$O: disodium (2R,3S)-1-((benzyloxy) carbonyl)-2-(carboxymethyl)-3-methylazetidine-2-carboxylate di-hydrate RS-ZMOO: benzyl (2R,3S)-2-(2-hydroxyethyl)-2-(hydroxymethyl)-3-methylazetidine-1-carboxylate RS-ZMSS: benzyl (2R,3S)-3-methyl-2-(2-((methylsulfonyl)oxy)ethyl)-2-(((methylsulfonyl)oxy)methyl)azetidine-1-carboxylate SR-ZMDB: benzyl (3S,4R)-6-benzyl-3-methyl-1,6-diazaspiro[3.4]octane-1-carboxylate SR-MDOZ: benzyl (3S,4R)-3-methyl-1,6-diazaspiro[3.4] octane-l1-carboxylate SR-MDOZ-OX: benzyl (3S,4R)-3-methyl-1,6-diazaspiro [3.4]octane-1-carboxylate oxalate SR-MDPZ: benzyl (3S,4R)-3-methyl-6-(7H-pyrrolo[2,3-d]pyrimidin-4-yl)-1,6-diazaspiro[3.4]octane-1-carboxylate SR-MDOP: 4-[(3S,4R)-3-methyl-1,6-diazaspiro[3.4]-octan-6-yl]-7H-pyrrolo[2,3-d]pyrimidine Compound A:

3-[(3S,4R)-3-methyl-6-(7H-pyrrolo[2,3-d]pyrimidin-4-yl)-1,6-diazaspiro[3.4]octan-1-γ 1]-3-oxopropanenitrile CPPY: 4-chloro-7H-pyrrolo[2,3-d]pyrimidine DPCN: 1-cyanoacetyl-3,5-dimethyl-1H-pyrazole TBBA: bromoacetic acid tert-butyl ester THF: tetrahydrofuran.

The measuring instruments and measuring conditions used are as follows.

$^1$H-NMR spectra were analyzed in CDCl$_3$ or DMSO-d$_6$ using tetramethylsilane as an internal standard, and all b values are shown as ppm. Unless otherwise indicated, a 400 MHz NMR instrument was used.

The symbols in the examples are meant as follows.

s: singlet d: doublet t: triplet q: quartet dd: double doublet ddd: double double doublet brs: broad singlet m: multiplet J: coupling constant The ion content in the samples was determined by averaging 3 observed data thereof.

Measuring instrument: Ion chromatograph LC-20 System (SHIMADZU)

Measuring condition: Electric-conductivity detector SHIMADZU CDD-10A VP

Column for anion analysis SHIMADZU SHIM-PAC IC-A3

Column for cation analysis SHIMADZU SHIM-PAC IC-C1

The water content in the samples was measured by Karl Fischer's method.

Measuring instrument: Karl Fischer Moisture Meter CA-06 (MITSUBISHI CHEMICAL)

Measuring condition:

Sample amount: about 20 mg

Reagent: Anode solution Aquamicron AX (API Corporation)

Catholyte Aquamicron CXU (API Corporation)

By elemental analysis, each weight % of carbon, hydrogen, and nitrogen in the samples was measured.

Step A. Preparation of S-MABB-HC (Compound 151)

[Chem. 2]

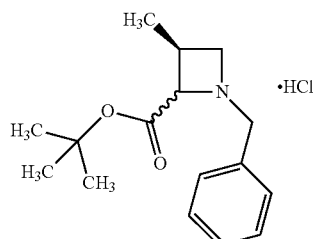

[5]

Step 1

[Chem. 3]

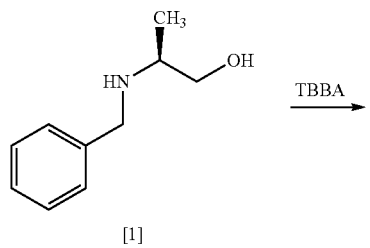

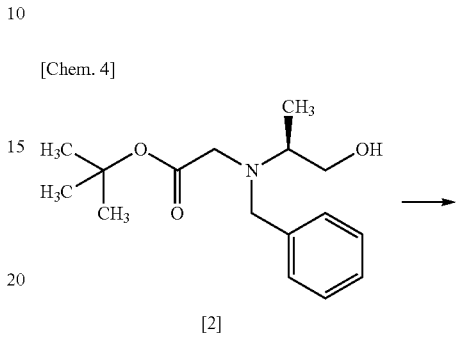

S-BAPO [11] (35.0 g, 212 mmol) was added to water (175 mL) at room temperature under nitrogen atmosphere. To the resulting suspension were added toluene (53 mL) and potassium carbonate (32.2 g, 233 mmol) at room temperature. To the resulting solution was added dropwise TBBA (434.4 g, 223 mmol) at room temperature, and then the used dropping funnel was washed with toluene (17 mL) and the washings were added to the reaction mixture. The reaction mixture was stirred at 65° C. for 21 hours, and then cooled to room temperature. After toluene (105 mL) was added to the reaction mixture and then the mixture was stirred, the organic layer was separated out. The organic layer was washed with water (175 mL), aqueous layer was removed, and then the solvent was removed out of the organic layer in vacuo. Toluene (105 mL) was added to the residue and the toluene solution was concentrated. The operation was repeated two more times to give a toluene solution of S-BBMO [2] (74.0 g, 212 mmol in theory). The given toluene solution of S-BBMO was used in the next step, assuming that the yield was 100%.

A crude product of S-BBMO which was prepared by the same process was evaporated to dryness and then measured about NMR and MS.

$^1$H-NMR (DMSO-$d_6$) δ: 7.36-7.13 (5H, m), 4.26 (1H, dd, J=6.8, 3.9 Hz), 3.72 (2H, dd, J=14.2, 6.8 Hz), 3.47-3.38 (1H, m), 3.30-3.08 (3H, m), 2.79 (1H, sext, J=6.8 Hz), 1.35 (9H, s), 0.96 (3H, d, J=6.8 Hz).

MS: m/z=280 [M+H]$^+$

Step 2

[Chem. 4]

To the toluene solution of S-BBMO [2] (74.0 g, 212 mmol) were added toluene (200 mL), tetrahydrofuran (35 mL), and then triethylamine (25.7 g, 254 mmol) at room temperature under nitrogen atmosphere. To the mixture was added dropwise methanesulfonyl chloride (26.7 g, 233 mmol) at 0° C., and then the used dropping funnel was washed with toluene (10 mL) and the washings were added to the reaction mixture. The reaction mixture was stirred at room temperature for 2 hours and further at 65° C. for 22 hours, and then cooled to room temperature. After sodium bicarbonate water (105 mL) was added to the reaction mixture and then the mixture was stirred, the organic layer was separated out. The organic layer was washed with water (105 mL), aqueous layer was removed, and then the solvent was removed out of the organic layer in vacuo. Toluene (105 mL) was added to the residue, and the toluene solution was concentrated. The operation was repeated two more times to give a toluene solution of R-BCAB [3] (75.3 g, 212 mmol in theory). The given toluene solution of R-BCAB was used in the next step, assuming that the yield was 100%.

A crude product of R-BCAB which was prepared by the same process was evaporated to dryness and then measured about NMR and MS. $^1$H-NMR (DMSO-$d_6$) δ: 7.28-7.11 (5H, m), 4.24-4.11 (1H, m), 3.80 (2H, d, J=3.6 Hz), 3.24 (2H, d, J=3.6 Hz), 2.98-2.78 (2H, m), 1.46-1.37 (12H, m).

MS: m/z=298 [M+H]$^+$

Step 3

[Chem. 5]

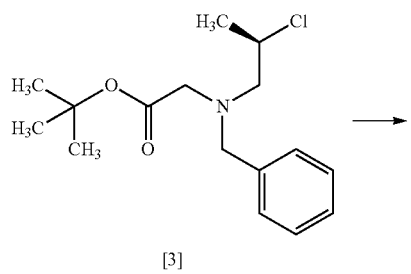

[3]

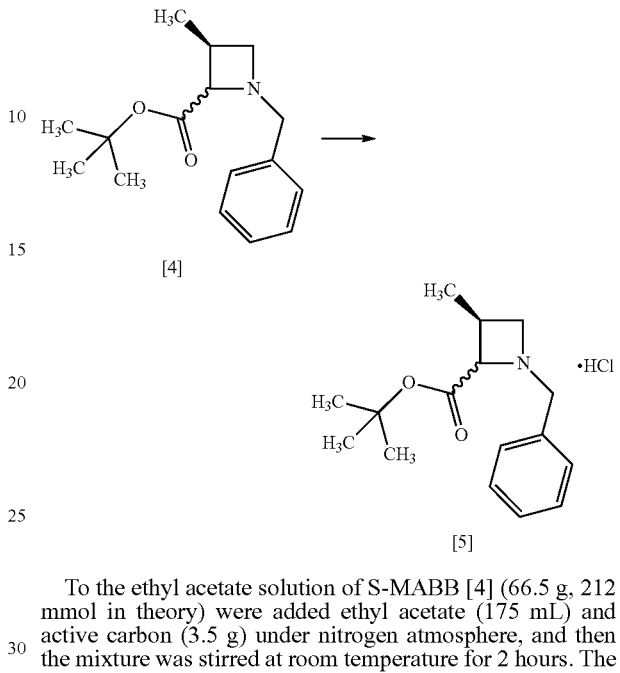

[4]

To the toluene solution of R-BCAB [3] (75.3 g, 212 mmol) were added tetrahydrofuran (88.0 mL) and 1,3-dimethyl-3,4,5,6-tetrahydro-2(1H)-pyrimidinone (42.0 mL) at room temperature under nitrogen atmosphere. To the resulting solution was added dropwise a solution of lithium bis(trimethylsilyl)amide/tetrahydrofuran (195 mL, 233 mmol) at 0° C., and then the used dropping funnel was washed with tetrahydrofuran (17.0 mL) and the washings were added to the reaction mixture. The reaction mixture was stirred at 0° C. for 1 hour, and then warmed to room temperature. After water (175 mL) and toluene (175 mL) were added to the reaction mixture and then the mixture was stirred, the organic layer was separated out. The resulting organic layer was washed with aqueous ammonium chloride (175 mL) and then water (175 mL), and the solvent was removed out of the organic layer in vacuo. Ethyl acetate (175 mL) was added to the residue and the ethyl acetate solution was concentrated. The operation was repeated two more times to give an ethyl acetate solution of S-MABB [4] (66.5 g, 212 mmol in theory). The given ethyl acetate solution of S-MABB was used in the next step, assuming that the yield was 100%.

A crude product of S-MABB which was prepared by the same process was evaporated to dryness and then measured about NMR and MS.

$^1$H-NMR (DMSO-d$_6$) b: 7.28-7.25 (10H, m), 3.75 (1H, d, J=12.7 Hz), 3.68 (1H, d, J=1.4 Hz), 3.66 (1H, d, J=6.7 Hz), 3.46 (2H, d, J=12.7 Hz), 3.30-3.17 (2H, m), 2.95 (1H, dd, J=6.2, 1.2 Hz), 2.77 (1H, dd, J=6.1, 2.2 Hz), 2.65-2.55 (1H, m), 2.48-2.40 (2H, m), 1.35 (9H, s), 1.35 (9H, s), 1.12 (3H, d, J=7.2 Hz), 1.09 (3H, d, J=6.2 Hz).

MS: m/z=262 [M+H]+

Step 4

[Chem. 6]

[5]

To the ethyl acetate solution of S-MABB [4] (66.5 g, 212 mmol in theory) were added ethyl acetate (175 mL) and active carbon (3.5 g) under nitrogen atmosphere, and then the mixture was stirred at room temperature for 2 hours. The active carbon was removed by filtration, and the residue on the filter was washed with ethyl acetate (175 mL). The washings were added to the filtrate. To the solution was added S-MABB-HC crystal (17.5 mg) that was prepared according to the method described herein at 0° C., and then 4 M hydrogen chloride/ethyl acetate (53.0 mL, 212 mmol) was dropped thereto at 0° C. The reaction mixture was stirred at 0° C. for 17 hours, and then the precipitated solid was collected on a filter, and washed with ethyl acetate (70 mL). The resulting wet solid was dried in vacuo to give S-MABB-HC [5] (48.3 g, 162 mmol, yield: 76.4%).

S-MABB-HC which was prepared by the same process was measured about NMR, MS, and Cl-content.

$^1$H-NMR (DMSO-d$_6$) δ: 11.08 (1H, br s), 10.94 (1H, br s), 7.52-7.42 (10H, m), 5.34 (1H, t, J=8.4 Hz), 4.90 (1H, br s), 4.45-4.10 (5H, m), 3.92-3.49 (3H, br m), 3.10-2.73 (2H, br m), 1.35 (9H, s), 1.29 (9H, s), 1.24 (3H, d, J=6.7 Hz), 1.17 (3H, d, J=7.4 Hz).

MS: m/z=262 [M+H-HCl]+

Cl content (ion chromatography): 11.9% (in theory: 11.9%).

Step B. Preparation of S-MACB-HC (Compound 161)

[Chem. 7]

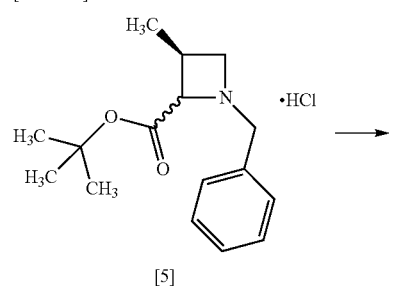

[5]

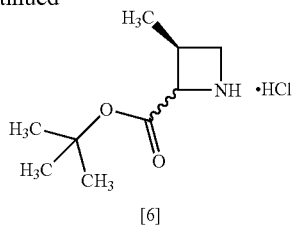

To a solution of S-MABB-HC [5] (5.0 g, 16.8 mmol) in methanol (15.0 mL) was added 5% palladium carbon (made by Kawaken Fine Chemicals Co., Ltd., PH type, 54.1% water-content 1.0 g) at room temperature under nitrogen atmosphere. The reaction vessel was filled with hydrogen, the reaction mixture was stirred at hydrogen pressure of 0.4 MPa at room temperature for 12 hours, the hydrogen in the reaction vessel was replaced with nitrogen, and then the 5% palladium carbon was removed by filtration. The reaction vessel and the 5% palladium carbon were washed with methanol (10 mL). The washings were added to the filtrate to give a methanol solution of S-MACB-HC [6] (24.8 g, 16.8 mmol in theory). The given methanol solution of SMACB-HC was used in the next step, assuming that the yield was 100%.

A crude product of S-MACB-HC which was prepared by the same process was evaporated to dryness and then measured about NMR and MS.

$^1$H-NMR (DMSO-$d_6$) δ: 9.60 (br s, 1H), 4.97 (d, 1H, J=9.2 Hz), 4.61 (d, 1H, J=8.4 Hz), 4.01 (dd, 1H, J=10.0, 8.4 Hz), 3.78-3.74 (m, 1H), 3.54 (dd, 1H, J=9.6, 8.4 Hz), 3.35 (dd, 1H, J=10.0, 6.0 Hz), 3.15-3.03 (m, 1H), 3.00-2.88 (m, 1H), 1.49 (s, 9H), 1.47 (s, 9H), 1.22 (d, 3H, J=6.8 Hz), 1.14 (d, 3H, J=7.2 Hz).

MS: m/z=172 [M+H]$^+$ (free form)

Step C. Preparation of S-ZMAB (Compound [7])

[Chem. 8]

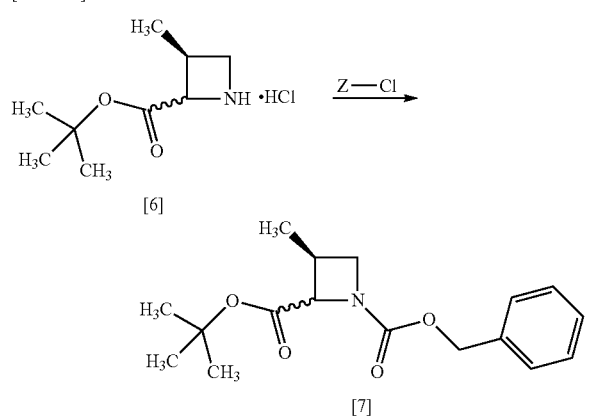

To the methanol solution of S-MACB-HC [6] (24.8 g, 16.8 mmol in theory) was added dropwise N,N-diisopropylethylamine (4.8 g, 36.9 mmol) at room temperature under nitrogen atmosphere, and then the used dropping funnel was washed with tetrahydrofuran (2.5 mL) and the washings were added to the reaction mixture. To the resulting reaction mixture was added dropwise benzyl chloroformate (3.0 g, 17.6 mmol) at 0° C., and then the used dropping funnel was washed with tetrahydrofuran (2.5 mL) and the washings were added to the reaction mixture. The reaction mixture was stirred at 0° C. for 1 hour, and then the solvent was removed in vacuo. After toluene (25.0 mL) and an aqueous solution of citric acid (25.0 mL) was added to the residue and then the mixture was stirred, the organic layer was separated out. The resulting organic layer was washed with sodium bicarbonate water (25.0 mL) and then water (25.0 mL), and the solvent in the organic layer was removed out of the organic layer in vacuo. Toluene (15.0 mL) was added to the residue and the toluene solution was concentrated. The operation was repeated one more time to give a toluene solution of S-ZMAB [7] (6.9 g, 16.8 mmol in theory). The given toluene solution of S-ZMAB was used in the next step, assuming that the yield was 100%.

A crude product of S-ZMAB which was prepared by the same process was evaporated to dryness and then measured about NMR and MS.

$^1$H-NMR (CDCl$_3$) δ: 7.38-7.28 (m, 10H), 5.16-5.04 (m, 4H), 4.60 (d, 1H, J=9.2 Hz), 4.18-4.12 (m, 2H), 4.04 (t, 1H, J=8.6 Hz), 3.66 (dd, 1H, J=7.6, 7.2 Hz), 3.50 (dd, 1H, J=8.0, 5.2 Hz), 3.05-2.94 (m, 1H), 2.60-2.50 (m, 1H), 1.43 (br s, 18H), 1.33 (d, 3H, J=6.5 Hz), 1.15 (d, 3H, J=7.2 Hz).

MS: m/z=328 [M+Na]$^+$.

Step D. Preparation of RS-ZMBB (Compound 181)

[Chem. 9]

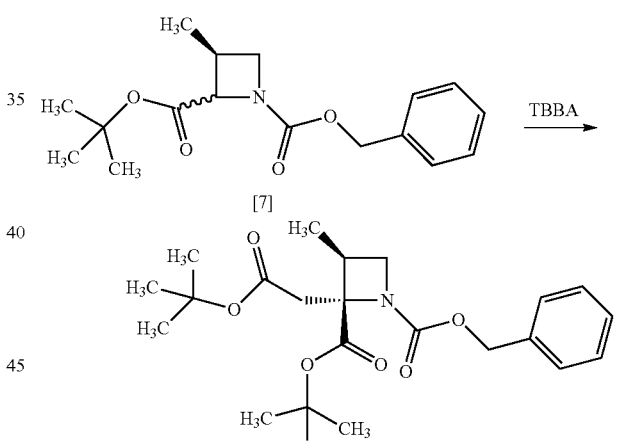

To the toluene solution of S-ZMAB [7] (6.9 g, 16.8 mmol) was added tetrahydrofuran (15.0 mL) at room temperature under nitrogen atmosphere. A solution of lithium bis(trimethylsilyl)amide/tetrahydrofuran (14.7 mL, 17.6 mmol) was added dropwise to the toluene solution at −70° C. The used dropping funnel was washed with tetrahydrofuran (2.5 mL) and the washings were added to the reaction mixture. The reaction mixture was stirred at −70° C. for 6 hours, and then a solution of TBBA (3.4 g, 17.6 mmol) in tetrahydrofuran (2.5 mL) was added dropwise to the reaction mixture at −70° C. The used dropping funnel was washed with tetrahydrofuran (2.5 mL) and the washings were added to the reaction mixture. The reaction mixture was stirred at −70° C. for 1 hour, and then warmed to room temperature. To the reaction mixture were added an aqueous ammonium chloride (25 mL) and toluene (25 mL) and then the mixture was stirred, the organic layer was separated out. The resulting organic layer was washed with an aqueous solution of citric acid (25 mL, ×2), sodium bicarbonate water (25 mL), and then water (25 mL), and then the solvent was removed out of the organic layer in vacuo. Acetonitrile (15 mL) was added to the residue and the acetonitrile solution was concentrated. The operation was repeated two more times. Acetonitrile (15 mL) and active carbon (0.25 g) were added to the residue, the mixture was stirred at room temperature for 2 hours. The active carbon was removed by filtration, and the reaction vessel and the residue on the filter was washed with acetonitrile (10 mL). The washings were added to the filtration, and then the filtration was concentrated in vacuo to give an acetonitrile solution of RS-ZMBB [8] (13.2 g, 16.8 mmol in theory). The given acetonitrile solution of RS-ZMBB was used in the next step, assuming that the yield was 100%.

A crude product of RS-ZMBB which was prepared by the same process was evaporated to dryness and then measured about NMR and MS.

$^1$H-NMR (DMSO-d$_6$) δ: 7.38-7.29 (m, 5H), 5.09-4.96 (m, 2H), 3.91 (t, 0.4H, J=8.0 Hz), 3.79 (t, 0.6H, J=8.0 Hz), 3.55 (t, 0.4H, J=7.2 Hz), 3.46 (t, 0.6H, J=7.5 Hz), 3.14-3.04 (m, 1H), 2.83-2.72 (m, 2H), 1.38 (br s, 9H), 1.37 (br s, 3.6H), 1.34 (br s, 5.4H), 1.12-1.09 (m, 3H).

MS: m/z=420 [M+H]$^+$.

Step E. Preparation of RS-ZMAA-DN.2H$_2$O (Compound [9])

[Chem. 10]

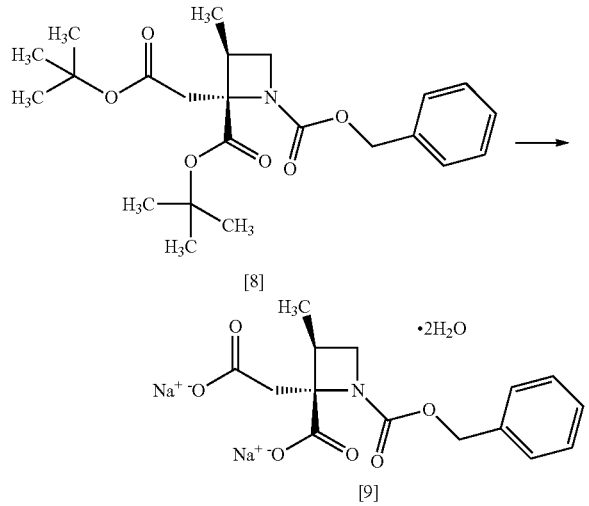

To the acetonitrile solution of RS-ZMBB [8] (13.2 g, 16.8 mmol in theory) was added acetonitrile (15 mL) at room temperature under nitrogen atmosphere. p-Toluenesulfonic acid mono-hydrate (6.4 g, 33.6 mmol) was added to the solution at room temperature. The reaction mixture was stirred at 50° C. for 12 hours, and then cooled to room temperature, and water (7.5 mL) was added dropwise to the reaction mixture. The reaction mixture was cooled to 0° C., and then 4 mol/L aqueous sodium hydroxide (17.6 mL, 70.5 mmol) was added dropwise thereto. After stirring the reaction mixture at room temperature for 1 hour, acetonitrile (75 mL) was added dropwise thereto at room temperature, and the reaction mixture was stirred for 3 hours. The precipitated solid was collected on a filter, and washed with a mixture of acetonitrile:water=4:1 (10 mL) and then acetonitrile (10 mL). The resulting wet solid was dried in vacuo to give RS-ZMAA-DN.2H$_2$O [9] (5.2 g, 13.4 mmol, yield: 85.4%).

RS-ZMAA-DN.2H$_2$O which was prepared by the same process was measured about NMR, MS, Na-content, and water-content.

$^1$H-NMR (DMSO-d$_6$) δ: 7.32-7.22 (m, 5H), 4.97 (d, 1H, J=12.7 Hz), 4.84 (d, 1H, J=12.7 Hz), 3.79 (t, 1H, J=8.0 Hz), 3.29 (d, 1H, J=14.8 Hz), 3.16-3.12 (m, 1H), 2.17-2.09 (m, 2H), 1.07 (d, 3H, J=6.9 Hz).

MS: m/z=352 [M+H]$^+$ (anhydrate)

Na content (ion chromatography): 13.3% (after correction of water content)(13.1% in theory)

Water content (Karl Fischer's method): 9.8% (9.3% in theory)

Step F. Preparation of RS-ZMAA (Compound [10])

[Chem. 11]

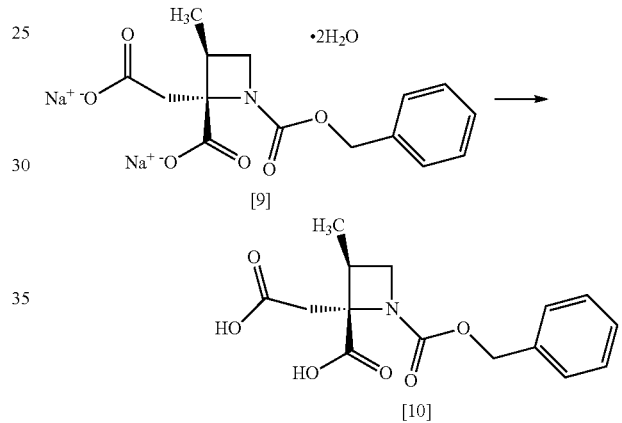

To 1 mol/L hydrochloric acid (180 mL) were added RS-ZMAA-DN.2H$_2$O [9] (30 g, 77.5 mmol) and acetonitrile (60 mL), and the mixture was stirred at room temperature for about 15 minutes. After ethyl acetate (240 mL) was added to the reaction mixture and then the mixture was stirred, the organic layer was separated out. The organic layer was washed with 10% brine (60 mL×2). The organic layer was stirred with magnesium sulfate (6 g), the magnesium sulfate was removed by filtration, and the residue on the filter was washed with ethyl acetate (60 mL). The filtrate and the washings are combined, and the solvent was removed out in vacuo. Tetrahydrofuran (240 mL) was added to the residue and the tetrahydrofuran solution was concentrated. The operation was repeated two more times. Tetrahydrofuran (60 mL) was added to the residue to give a tetrahydrofuran solution of RS-ZMAA [10]. The given tetrahydrofuran solution of RS-ZMAA was used in the next step, assuming that the yield was 100%.

RS-ZMAA which was prepared by the same process was measured about NMR and MS.

$^1$H-NMR (DMSO-D$_6$) δ: 7.35-7.28 (m, 5H), 5.06-4.94 (m, 2H), 3.86 (dt, 1H, J=48.4, 7.9 Hz), 3.50 (dt, 1H, J=37.9, 7.4 Hz), 3.16-3.02 (br m, 1H), 2.91-2.77 (br m, 2H), 1.08 (d, 3H, J=6.9 Hz)

MS: m/z=308 [M+H]$^+$.

Step G. Preparation of RS-ZMOO (Compound [11])

[Chem. 12]

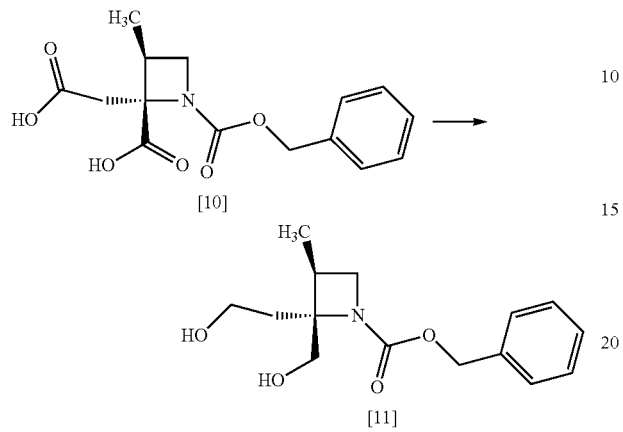

To the tetrahydrofuran solution of RS-ZMAA [10] (25.8 mmol in theory) was added tetrahydrofuran (50 mL) under nitrogen atmosphere. Boron trifluoride etherate complex (4.40 g) was added dropwise thereto at 0° C. to 5° C. The used dropping funnel was washed with tetrahydrofuran (5 mL) and the washings were added to the reaction mixture. To the reaction mixture was added dropwise 1.2 mol/L borane-tetrahydrofuran complex (43.0 mL) at 0° C. to 5° C., and the reaction mixture was stirred at 0° C. to 5° C. for about 30 minutes, and then further stirred at room temperature overnight. To the reaction mixture was added dropwise 1.2 mol/L borane-tetrahydrofuran complex (21.1 mL) at 0° C. to 5° C., and then the reaction mixture was stirred at room temperature overnight. After stirring, water (40 mL) was added dropwise to the reaction mixture at 0° C. to 15° C. To the reaction mixture was added sodium bicarbonate (5.42 g) at 0° C. to 15° C. The sodium bicarbonate left in the vessel was washed with water (10 mL), and the washings were added to the reaction mixture. The reaction mixture was stirred at room temperature for 2 hours, and then toluene (50 mL) was added thereto and the reaction mixture was further stirred. The organic layer was separated out. The resulting organic layer was washed with 10% brine (20 mL×1), a mixture (×3) of 5% sodium bicarbonate water (20 mL) and 10% brine (20 mL), a mixture (×1) of 5% aqueous potassium hydrogensulfate (10 mL) and 10% brine (10 mL), and then 10% brine (20 mL×2). The organic layer was stirred with magnesium sulfate (8.9 g), the magnesium sulfate was removed by filtration, and the residue on the filter was washed with toluene (20 mL). The washings were added to the filtration, and then the filtrate was concentrated in vacuo. To the concentrated residue was added toluene (80 mL). The solution was concentrated in vacuo, and toluene (15 mL) was added thereto to give a toluene solution of RS-ZMOO [11]. The given toluene solution of RS-ZMOO was used in the next step, assuming that the yield was 100%. RS-ZMOO which was prepared by the same process was measured about NMR and MS.

$^1$H-NMR (CDCl$_3$) b: 7.39-7.30 (m, 5H), 5.10 (s, 2H), 4.15-4.01 (br m, 2H), 3.83-3.73 (br m, 3H), 3.48 (dd, 1H, J=8.3, 6.4 Hz), 2.59-2.50 (br m, 1H), 2.46-2.40 (br m, 1H), 2.07-1.99 (m, 1H), 1.14 (d, 3H, J=7.2 Hz)

MS: m/z=280 [M+H]+.

Step H. Preparation of RS-ZMSS (Compound [12])

[Chem. 13]

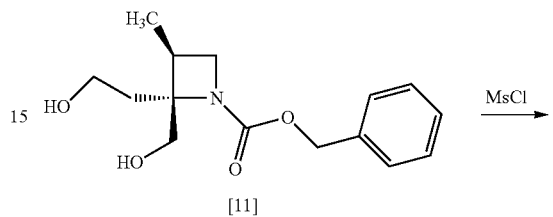

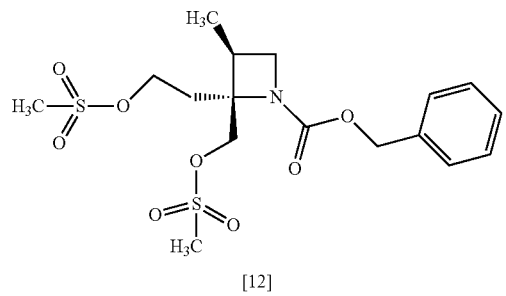

To the toluene solution of RS-ZMOO [11] (23.7 mmol in theory) was added toluene (55 mL) under nitrogen atmosphere. And, triethylamine (5.27 g) was added dropwise thereto at −10° C. to 10° C., and the used dropping funnel was washed with toluene (1.8 mL) and the washings were added to the reaction mixture. To this reaction mixture was added dropwise methanesulfonyl chloride (5.69 g) at −10° C. to 10° C., and then the used dropping funnel was washed with toluene (1.8 mL) and the washings were added to the reaction mixture. The reaction mixture was stirred at 0° C. to 10° C. for about 2 hours, and then water (28 mL) was added dropwise thereto at 0° C. to 20° C. The reaction mixture was stirred at 0° C. to 20° C. for about 30 minutes, and then, the organic layer was separated out. The resulting organic layer was washed twice with 10% brine (18 mL). The organic layer was stirred with magnesium sulfate (2.75 g), the magnesium sulfate was removed by filtration, and the residue on the filter was washed with toluene (18 mL). The washings were added to the filtrate, and then the solvent was removed from the filtrate in vacuo. To the concentrated residue was added toluene up to 18 mL to give a toluene solution of RS-ZMSS [12]. The given toluene solution of RS-ZMSS was used in the next step, assuming that the yield was 100%.

RS-ZMSS which was prepared by the same process was measured by NMR and MS. $^1$H-NMR (DMSO-D$_6$) b: 7.37-7.27 (br m, 5H), 5.10-4.98 (m, 2H), 4.58-4.22 (br m, 4H), 3.84 (dt, 1H, J=45.6, 8.1 Hz), 3.48-3.33 (br m, 1H), 3.17-3.10 (m, 6H), 2.81-2.74 (br m, 1H), 2.22-2.12 (m, 2H)

MS: m/z=436 [M+H]$^+$.

Step I. Preparation of SR-ZMDB (Compound [13])

[Chem. 14]

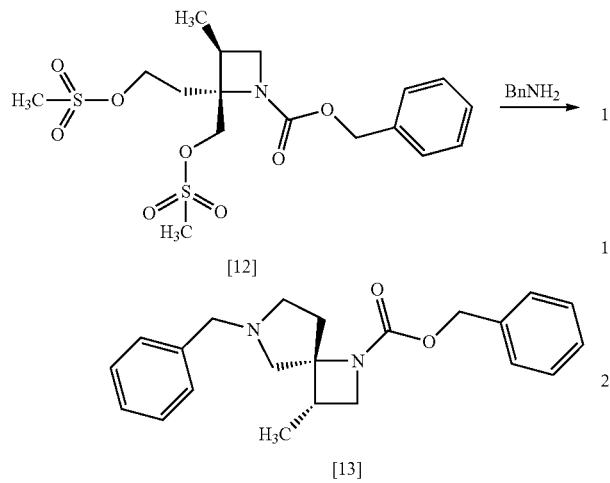

[12]

[13]

To a toluene solution of RS-ZMSS [12] (23.7 mmol in theory) was added toluene (55 mL) under nitrogen atmosphere. And, benzylamine (17.8 g) was added dropwise thereto at room temperature, and the used dropping funnel was washed with toluene (9.2 mL) and the washings were added to the reaction mixture. The reaction mixture was stirred at room temperature for about 1 hour, at 55° C. to 65° C. for about 3 hours, and then at 70° C. to 80° C. for 6 hours. After the reaction mixture was cooled to room temperature, 10% NaCl (28 mL) was added dropwise thereto, and the reaction mixture was stirred at room temperature for about 30 minutes. After toluene (37 mL) was added to the reaction mixture and then the mixture was stirred, the organic layer was separated out. The resulting organic layer was washed with a mixture (×2) of 10% brine (18 mL) and acetic acid (2.84 g), and then 10% brine (11 mL, ×1). The solvent of the organic layer was removed in vacuo to a half volume, and acetic anhydride (1.45 g) was added to the concentrated residue at room temperature. The mixture was stirred for about 3 hours. To the reaction mixture were added dropwise a solution of potassium hydrogensulfate (3.87 g) and water (92 mL) at room temperature. The reaction mixture was stirred, and then the aqueous layer was separated out. The resulting aqueous layer was washed with toluene (18 mL), and toluene (73 mL) and then sodium bicarbonate (6.56 g) were added to the aqueous layer at room temperature, and the mixture was stirred. The organic layer was separated out, and washed with 10% brine (11 mL). The organic layer was stirred with magnesium sulfate (2.75 g), the magnesium sulfate was removed by filtration. The residue on the filter was washed with toluene (18 mL), and the washings were added to the filtrate, and then the filtrate was concentrated in vacuo. Toluene (44 mL) was added to the concentrated residue to give a toluene solution of SR-ZMDB [13]. The given toluene solution of SR-ZMDB was used in the next step, assuming that the yield was 100%.

$^{1}$H-NMR (CDCl$_3$) b: 7.35-7.20 (m, 10H), 5.08 (d, 2H, J=23.6 Hz), 3.94 (q, 1H, J=7.9 Hz), 3.73-3.42 (br m, 2H), 3.30-3.23 (m, 1H), 3.05 (dd, 1H, J=19.7, 9.5 Hz), 2.79 (dt, 1H, J=69.6, 6.1 Hz), 2.57-2.32 (br m, 4H), 1.96-1.89 (m, 1H), 1.09 (d, 3H, J=6.9 Hz)

MS: m/z=351 [M+H]$^{+}$.

Step J. Preparation of SR-MDOZ (Compound [14])

[Chem. 15]

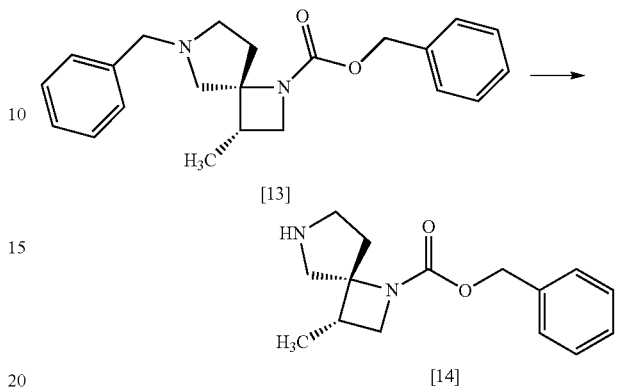

[13]

[14]

To a solution of 1-chloroethyl chloroformate (3.72 g) in toluene (28 mL) was added dropwise the toluene solution of SR-ZMDB [13] (23.7 mmol in theory) at 0° C. to 10° C. under nitrogen atmosphere, and then the used dropping funnel was washed with toluene (4.6 mL) and the washings were added to the reaction mixture. To the reaction mixture was added triethylamine (718 mg) at 0° C. to 10° C., and the reaction mixture was stirred at 15° C. to 25° C. for about 2 hours. Then, methyl alcohol (46 mL) was added to the reaction mixture, and the mixture was stirred at 50° C. to 60° C. for additional about 2 hours. The solvent of the reaction mixture was removed in vacuo to a volume of about less than 37 mL. To the concentrated residue was added dropwise 2 mol/L hydrochloric acid (46 mL) at 15° C. to 20° C., and the mixture was stirred, and the aqueous layer was separated out. The resulting aqueous layer was washed with toluene (28 mL, ×2). To the aqueous layer were added 20% brine (46 mL) and tetrahydrofuran (92 mL), and then 8 mol/L aqueous sodium hydroxide (18 mL) was added dropwise thereto at 0° C. to 10° C. The organic layer was separated out from the reaction mixture, washed with 20% brine (18 mL, ×2), and then the solvent of the organic layer was removed in vacuo. To the concentrated residue was added tetrahydrofuran (92 mL), and the solution was concentrated in vacuo. The operation was repeated one more time. The concentrated residue was dissolved in tetrahydrofuran (92 mL). The solution was stirred with magnesium sulfate (2.75 g), and the magnesium sulfate was removed by filtration. The residue on the filter was washed with tetrahydrofuran (28 mL), the washings were added to the filtrate, and the filtrate was concentrated in vacuo. The volume of the concentrated residue was adjusted to about 20 mL with tetrahydrofuran to give a tetrahydrofuran solution of SR-MDOZ [14] (net weight: 4.01 g, 15.4 mol, yield: 65.0%).

SR-MDOZ which was prepared by the same process was evaporated to dryness and then measured about NMR and MS.

$^{1}$H-NMR (CDCl$_3$) δ: 7.37-7.28 (m, 5H), 5.08 (dd, 2H, J=16.8, 12.8 Hz), 4.00 (dd, 1H, J=17.1, 8.3 Hz), 3.40-3.31 (m, 1H), 3.24 (d, 1H, J=12.7 Hz), 3.00 (dd, 1H, J=54.9, 12.4 Hz), 2.87-2.57 (m, 3H), 2.47-2.27 (m, 1H), 1.91-1.80 (m, 1H), 1.14 (d, 3H, J=7.2 Hz)

MS: m/z=261 [M+H]$^{+}$.

Step K. Preparation of SR-MDOZ-OX (Compound [15])

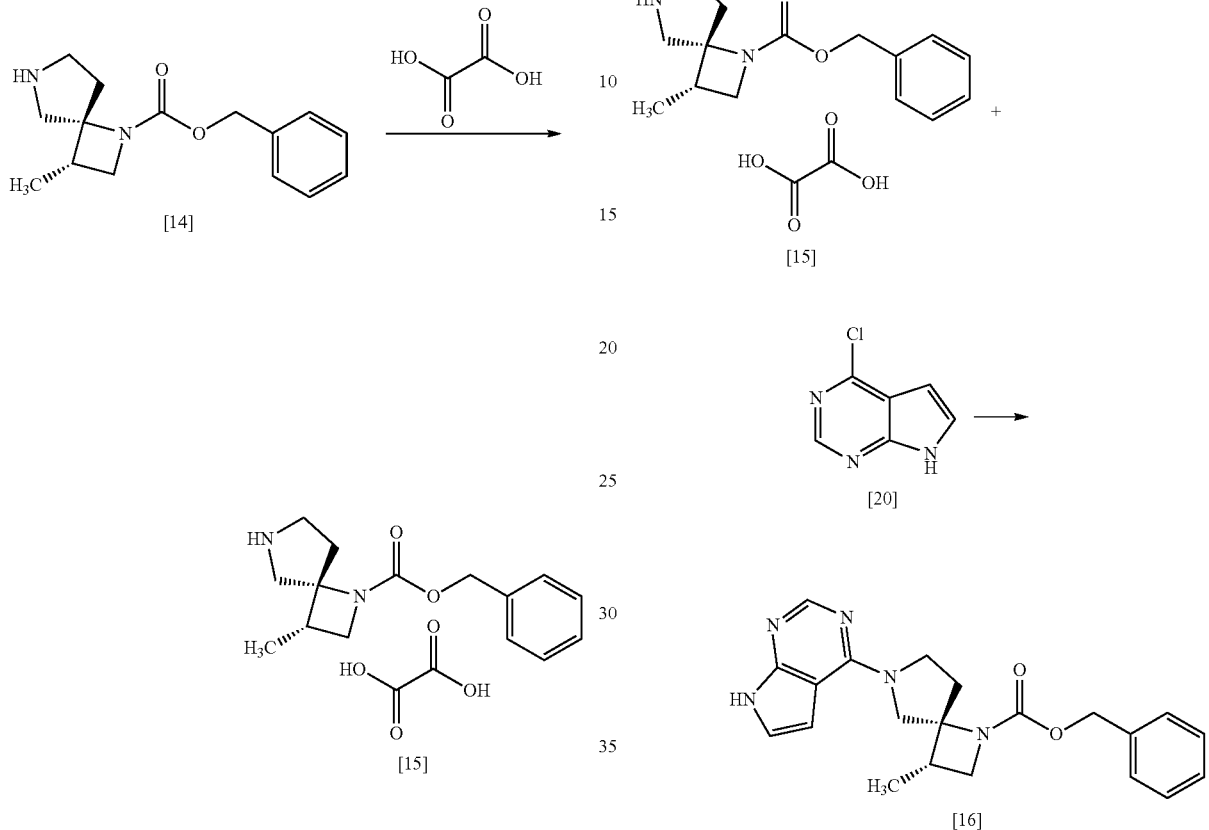

Step L. Preparation of SR-MDPZ (Compound [16])

Under nitrogen atmosphere, oxalic acid (761 mg) was dissolved in tetrahydrofuran (40 mL), and the tetrahydrofuran solution of SR-MDOZ [14] (3.84 mmol in theory) was added dropwise to the solution of oxalic acid at room temperature. To the solution was added SR-MDOZ-OX crystal (1 mg) that was prepared according to the method described herein at room temperature, and the mixture was stirred at room temperature for about 3.5 hours to precipitate the crystal. To the slurry solution was added dropwise the tetrahydrofuran solution of SR-MDOZ (3.84 mmol) at room temperature, and the mixture was stirred at room temperature for about 1 hour. The slurry solution was heated, and stirred at 50° C. to 60° C. for about 2 hours, and then stirred at room temperature overnight. The slurry solution was filtrated, and the wet crystal on the filter was washed with tetrahydrofuran (10 mL), dried in vacuo to give SR-MDOZ-OX [15] (2.32 g, 6.62 mol, yield: 86.2%).

SR-MDOZ-OX which was prepared by the same process was measured about NMR, MS, and elementary analysis.

$^1$H-NMR (DMSO-D$_6$) b: 7.37-7.30 (m, 5H), 5.15-5.01 (m, 2H), 3.92 (dt, 1H, J=43.5, 8.4 Hz), 3.48-3.12 (br m, 5H), 2.67-2.56 (m, 1H), 2.46-2.35 (m, 1H), 2.12-2.05 (m, 1H), 1.13 (d, 3H, J=6.9 Hz)

MS: m/z=261 [M+H]$^+$ elementary analysis: C 58.4 wt %, H 6.4 wt %, N 7.9% wt % (theoretically, C 58.3 wt %, H 6.3 wt %, N 8.0 wt %)

To SR-MDOZ-OX [15] (12.0 g, 34.2 mmol) were added ethanol (36 mL), water (72 mL), CPPY [20] (5.36 g, 34.9 mmol), and then K$_3$PO$_4$ (21.8 g, 103 mmol) under nitrogen atmosphere. The reaction mixture was stirred at 80° C. for 5 hours, and then cooled to 40° C. Toluene (120 mL) was added thereto at 40° C., and the organic layer was separated out. The resulting organic layer was washed with 20% aqueous potassium carbonate (48 mL), followed by washing twice with water (48 mL). The solvent of the organic layer was then removed in vacuo. tert-butanol (60 mL) was added to the residue and the tert-butanol solution was concentrated. The operation was repeated two more times. tert-Butanol (36 mL) was added to the concentrated residue to give a solution of SR-MDPZ [16] in tert-butanol (61.1 g, 34.2 mmol in theory). The given tert-butanol solution of SR-MDPZ was used in the next step, assuming that the yield was 100%.

SR-MDPZ which was prepared by the same process was isolated as a solid from a mixture of ethyl acetate and n-heptane, and then measured about NMR and MS.

$^1$H-NMR (DMSO-d$_6$) δ: 11.59 (br s, 1H), 8.08 (s, 1H), 7.41-7.26 (br m, 3H), 7.22-7.08 (br m, 3H), 6.64-6.51 (br m, 1H), 5.07-4.91 (br m, 2H), 4.09-3.67 (br m, 5H), 3.47-3.32 (br m, 1H), 2.67-2.55 (br m, 2H), 2.21-2.15 (br m, 1H), 1.11 (d, 3H, J=6.9 Hz).

MS: m/z=378 [M+H]$^+$

Step M. Preparation of SR-MDOP (Compound [17])

[Chem. 18]

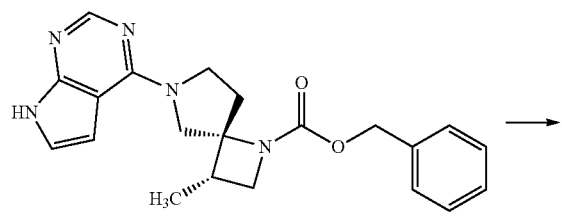

[16]

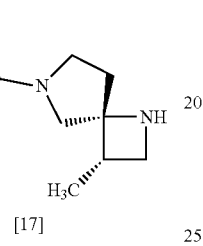

[17]

To the solution of SR-MDPZ [16] in tert-butanol (34.2 mmol in theory) were added ammonium formate (10.8 g, 171 mmol), water (60 mL), and 10% palladium carbon (made by Kawaken Fine Chemicals Co., Ltd., M type, 52.6% water-content, 1.20 g) under nitrogen atmosphere. The reaction mixture was stirred at 40° C. for 13 hours, and then cooled to room temperature, and the resulting precipitate was removed by filtration. The reaction vessel and the residue on the filter were washed with tert-butanol (24 mL), the washings was added to the filtrate, and 8 M aqueous sodium hydroxide (25.7 mL, 205 mmol) and sodium chloride (13.2 g) were added to the filtrate. The reaction mixture was stirred at 50° C. for 2 hours, and then toluene (84 mL) was added thereto at room temperature, and the organic layer was separated out. The resulting organic layer was washed with 20% brine (60 mL), stirred with anhydrous sodium sulfate, and then the sodium sulfate was removed by filtration. The residue on the filter was washed with a mixture of toluene: tert-butanol=1:1 (48 mL), the washings was added to the filtrate, and the filtrate was concentrated in vacuo. To the concentrated residue was added toluene (60 mL), and the solution was stirred at 50° C. for 2 hours, and then the solvent was removed in vacuo. To the concentrated residue was added toluene (60 mL) again, and the solution was concentrated. To the concentrated residue was added toluene (48 mL), and the solution was stirred at room temperature for 1 hour, and then at ice temperature for 1 hour. The precipitated solid was collected on a filter, and washed with toluene (24 mL). The resulting wet solid was dried in vacuo to give SR-MDOP [17] (7.07 g, 29.1 mmol, yield: 84.8%). SR-MDOP which was prepared by the same process was measured about NMR and MS.

$^1$H-NMR (DMSO-d$_6$) δ: 11.57 (br s, 1H), 8.07 (s, 1H), 7.10 (d, 1H, J=3.2 Hz), 6.58 (d, 1H, J=3.2 Hz), 3.92-3.59 (br m, 4H), 3.49 (dd, 1H, J=8.3, 7.2 Hz), 2.93 (dd, 1H, J=7.2, 6.1 Hz), 2.61-2.53 (m, 2H), 2.12-2.01 (br m, 2H), 1.10 (d, 3H, J=6.9 Hz).

MS: m/z=244 [M+H]$^+$.

Step N. Preparation of Compound A Mono-Ethanolate (Compound [18])

[Chem. 19]

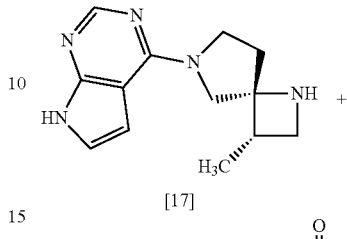

[17]

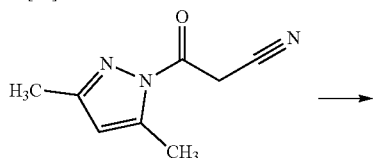

[21]

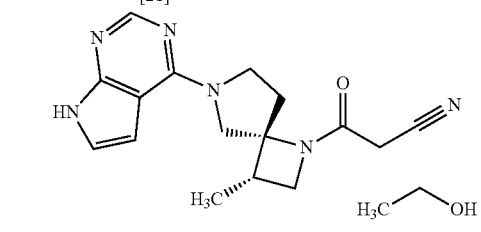

[18]

Under nitrogen atmosphere, acetonitrile (60 mL) and triethylamine (416 mg, 4.11 mmol) were added to SR-MDOP [17] (5.00 g, 20.5 mmol), and to the solution was added dropwise a solution of DPCN [21] (3.69 g, 22.6 mmol) in acetonitrile (35 mL) at 45° C., and then the used dropping funnel was washed with acetonitrile (5.0 mL) and the washings were added to the reaction mixture. The reaction mixture was stirred at 45° C. for 3 hours, and then cooled to room temperature. After 5% sodium bicarbonate water (25 mL), 10% brine (25 mL), and ethyl acetate (50 mL) were added to the reaction mixture and then the mixture was stirred, the organic layer was separated out. The solvent of the organic layer was removed out in vacuo. Tetrahydrofuran (50 mL) was added to the residue and the tetrahydrofuran solution was concentrated. The operation was repeated three more times. To the concentrated residue was added tetrahydrofuran (50 mL), and water was added the solution to adjust the water content to 5.5%. The resulting precipitate was removed by filtration. The reaction vessel and the residue on the filter were washed with tetrahydrofuran (15 mL), the washings were added to the filtrate, and the solvent was removed out of the filtrate in vacuo. To the concentrated residue were added ethanol (50 mL) and Compound A crystal (5.1 mg) that was prepared according to the method described in the following Example 15. The mixture was stirred at room temperature for 1 hour, and concentrated in vacuo. To the residue was ethanol (50 mL), and the solution was concentrated again. To the concentrated residue was added ethanol (15 mL), and the solution was stirred at room temperature for 1 hour. The precipitated solid was collected on the filter, and washed with ethanol (20 mL). The resulting wet solid was dried in vacuo to give Compound A mono-ethanolate [18] (6.26 g, 17.6 mmol, yield: 85.5%).

Compound A mono-ethanolate which was prepared by the same process was measured by NMR and MS.

$^1$H-NMR (DMSO-d$_6$) δ: 11.59 (br s, 1H), 8.08 (s, 1H), 7.11 (dd, 1H, J=3.5, 2.3 Hz), 6.58 (dd, 1H, J=3.5, 1.8 Hz), 4.34 (t, 1H, J=5.1 Hz), 4.16 (t, 1H, J=8.3 Hz), 4.09-3.92 (m, 3H), 3.84-3.73 (m, 1H), 3.71 (d, 1H, J=19.0 Hz), 3.65 (d, 1H, J=19.0 Hz), 3.58 (dd, 1H, J=8.2, 5.9 Hz), 3.44 (dq, 2H, J=6.7, 5.1 Hz), 2.69-2.60 (m, 2H), 2.23-2.13 (br m, 1H), 1.12 (d, 3H, J=7.1 Hz), 1.06 (t, 3H, J=6.7 Hz).

MS: m/z=311 [M+H]$^+$

Step O. Purification of Compound A (Compound [19])

[Chem. 20]

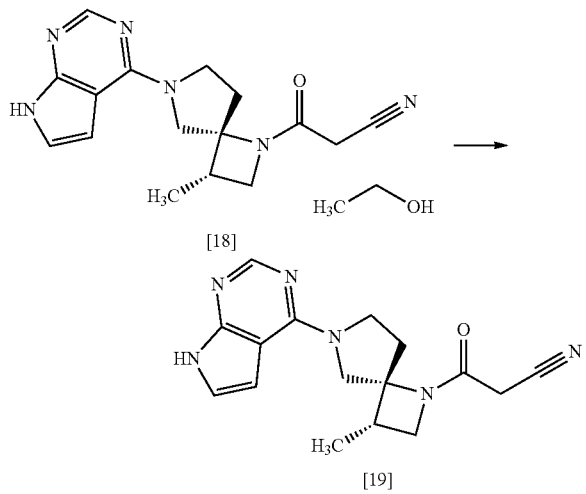

Compound A mono-ethanolate [18] (4.00 g, 11.2 mmol) and n-butanol (32 mL) were mixed under nitrogen atmosphere, and the mixture was dissolved at 110° C. The mixture was cooled to 85° C., and Compound A crystal (4.0 mg) that was prepared according to the method described herein was added thereto, and the mixture was stirred at 85° C. for 2 hours, at 75° C. for 1 hour, and then at room temperature for 16 hours. The precipitated solid was collected on a filter, and washed with n-butanol (8.0 mL) and then ethyl acetate (8.0 mL). The resulting wet solid was dried in vacuo to give Compound A [19] (3.18 g, 10.2 mmol, yield: 91.3%).

Compound A which was prepared by the same process was measured by NMR and MS.

$^1$H-NMR (DMSO-d$_6$) b: 11.59 (br s, 1H), 8.08 (s, 1H), 7.11 (dd, 1H, J=3.5, 2.5 Hz), 6.58 (dd, 1H, J=3.5, 1.8 Hz), 4.16 (t, 1H, J=8.3 Hz), 4.09-3.93 (m, 3H), 3.84-3.73 (m, 1H), 3.71 (d, 1H, J=19.0 Hz), 3.65 (d, 1H, J=19.0 Hz), 3.58 (dd, 1H, J=8.2, 5.9 Hz), 2.69-2.59 (m, 2H), 2.23-2.13 (m, 1H), 1.12 (d, 3H, J=7.2 Hz).

MS: m/z=311 [M+H]$^+$

Using Compound A, which was prepared by the same method, the single crystal X-ray analysis was carried out.

(1) Preparation of Single Crystal

To 10 mg of Compound A in a LaPha ROBO Vial® 2.0 mL wide-mouthed vial was added 0.5 mL of chloroform. The vial was covered with a cap, in which Compound A was completely dissolved. In order to evaporate the solvent slowly, a hole was made on the septum attached in the cap with a needle of a TERUMO® syringe, and the vial was still stood at room temperature. The resulting single crystal was used in the structural analysis.

(2) Measuring Instrument

Beam line: SPring-8 BL32B2

Detector: Rigaku R-AXIS V diffractometer (3) Measuring Method

The radiant light of 0.71068 Å was irradiated to the single crystal to measure X-ray diffraction data.

(4) Assay Method

Using the X-ray anomalous scattering effect of the chlorine atom in the resulting Compound A chloroform-solvate, the absolute configuration of Compound A was identified as (3S,4R). Based on the obtained absolute configuration of Compound A, the absolute configurations of each process intermediate were identified.

Characterization of Form α

X-Ray Powder Diffraction (XRPD)

Form α was characterized by XRPD using a Spectris Co., Ltd. PANalytical instrument Model Number: X'Pert Pro under the following data acquisition parameters.

TABLE 5

| | |
|---|---|
| Radiation | Cu-Kα$_1$/45 kV/40 mA |
| Counter Monochrometer | Graphite counter monochrometer |
| Scanning Range | 3.0 to 40.0° |
| Soller slit | 0.02 rad |
| Divergence slit | ½ |
| Anti-scatter slit | ½ |
| Mask | Mask Fixed 4 mm |
| Mode | Transmission |
| Optics | Focusing mirror |
| Wobble scan | Wobble axis: omega |
| | Number of step: 7 |
| | Step size: 1.000 |
| | Range: 6 |
| Sample holder | 96 well plate |
| Scan step time | 20 sec |
| Scan step | 0.00334° |

The XRPD pattern for Form α is shown in FIG. 1 and the corresponding data is provided below in Table 1-8.

TABLE 1-8

| Diffraction angle [2θ (°)] | Relative intensity [%] | Diffraction intensity [cps] |
|---|---|---|
| 7.8 | 33.39 | 3282.99 |
| 10.2 | 19.13 | 1880.69 |
| 11.4 | 11.24 | 1105.05 |
| 12.3 | 2.82 | 277.49 |
| 12.7 | 11.01 | 1082.97 |
| 13.4 | 12.90 | 1268.20 |
| 14.7 | 100.00 | 9832.97 |
| 15.9 | 20.81 | 2046.10 |
| 16.2 | 8.44 | 829.65 |
| 16.4 | 14.61 | 1436.83 |
| 17.1 | 8.78 | 863.45 |
| 17.9 | 61.50 | 6047.48 |
| 18.9 | 9.37 | 920.90 |
| 19.5 | 1.55 | 152.43 |
| 20.2 | 7.58 | 745.51 |
| 20.8 | 2.87 | 282.31 |
| 21.2 | 1.59 | 156.25 |
| 22.2 | 3.66 | 360.04 |
| 22.6 | 67.73 | 6659.41 |
| 22.9 | 17.99 | 1768.98 |
| 23.5 | 2.82 | 277.10 |
| 24.3 | 10.67 | 1048.90 |
| 24.8 | 5.71 | 561.67 |
| 25.6 | 10.68 | 1049.68 |
| 26.5 | 2.48 | 243.62 |

TABLE 1-8-continued

| Diffraction angle [2θ (°)] | Relative intensity [%] | Diffraction intensity [cps] |
|---|---|---|
| 27.0 | 47.44 | 4664.60 |
| 27.7 | 1.63 | 160.56 |
| 28.3 | 1.19 | 117.03 |
| 29.6 | 1.28 | 125.94 |
| 30.1 | 1.15 | 113.57 |
| 30.9 | 1.71 | 168.29 |
| 31.7 | 1.06 | 104.00 |
| 32.6 | 1.63 | 159.85 |
| 33.4 | 3.41 | 335.16 |
| 34.0 | 1.52 | 149.80 |
| 35.4 | 0.94 | 92.36 |
| 36.1 | 1.45 | 142.86 |
| 36.9 | 1.28 | 125.60 |
| 37.9 | 0.61 | 59.60 |
| 39.5 | 1.38 | 136.12 |

Differential Scanning Calorimetry (DSC)

DSC data was collected on a TA Instruments Model Number Q2000 instrument with the following parameters:
  Sample size: approximately, 3 mg
  Pan: sealed aluminum pan
  Range: 25-230° C.
  Heating Rate: 2° C./min under nitrogen gas flow.

The DSC thermogram for Form α is provided in FIG. 4, showing a single endothermic event having a peak of 188° C. and onset of 185° C.

Thermogravimetric Differential Thermal Analysis (TG-DTA)

TG-DTA data was collected on a Mettler Toledo Model Number: TGA/SDTA851e/SF instrument with the following parameters:
  Sample: approximately, 5 mg
  Range: 25-250° C.
  Heating Rate: 2° C./min under nitrogen gas flow.

The extrapolated onset temperature was 186.29° C. and the weight loss was not observed in the range of 25 and 220° C. TG-DTA data for Form α is shown in FIG. 7.

Solid State $^{13}$C NMR

Solid state $^{13}$C NMR data was collected on a Bruker BioSpin Corporation

AVANCE III 400 instrument with the following parameters:
  Probe: 4 mm CP/MAS probe
  Measurement temperature: room temperature
  Reference material: glycine (External standard: a peak of lower magnetic field was set on 176.03 ppm)
  Measurement core: $^{13}$C (100.6228303 MHz)
  Rotating speed: 14.3 kHz
  Pulse repetition time: 5 seconds
  Cumulated number: 3072 times
  Pulse mode: CP/MAS measurement Solid state $^{13}$C NMR data for Form α is presented in FIG. 10 showing peaks at: 14.8, 17.0, 24.5, 27.2, 35.0, 35.9, 38.6, 48.8, 49.5, 53.6, 78.3, 101.4, 103.0, 116.2, 118.0, 122.0, 122.7, 151.2, 154.8, 162.4, and 163.3 ppm.

Example 2

Preparation and Characterization of Compound A, Form β

Preparation

Compound A (3992.3 g, crystalline Form α), which had been passed through a sieve of 500 μm, was ground with a Spiral Jet Mill 100AS (manufactured by Hosokawa Micron Corporation) under the conditions below to give a ground product (3473.6 g) with Compound A (361.0 g) adhering to the nozzle-ring part.
  Grinding Conditions
  Gas used: nitrogen
  Grinding nozzle: 1.5 mm in diameter×4
  Ejector nozzle: 1.3 mm in diameter
  Air pressure for grinding: 0.50 to 0.60 MPa
  Air pressure for ejector: 0.50 to 0.60 MPa
  Rate for supplying Compound A: 8 g/min The Compound A (50.0 g, 161 mmol) adhering to the nozzle-ring part was added to a mixed solution of 1-butanol/acetonitrile (1:3 v/v) (250 mL), and the mixture was stirred at 40° C. for 10 days. The resulting suspension was cooled to room temperature and further stirred at room temperature for 24 hours. A precipitated crystalline material was collected on a filter. The collected crystalline product was washed with ethyl acetate (50 mL) twice and dried under reduced pressure at 40° C. to give Compound A, crystalline Form β (35.5 g, yield 71%).

Characterization

X-Ray Powder Diffraction

The XRPD pattern for Form β is shown in FIG. 2 and the corresponding data is provided below in Table 2-1. Instrument and data acquisition parameters are as described above in Example 1 for the characterization of Form α.

TABLE 2-1

| Diffraction angle [2θ (°)] | Relative intensity [%] | Diffraction intensity [cps] |
|---|---|---|
| 7.8 | 20.40 | 699.45 |
| 10.5 | 18.12 | 621.23 |
| 11.8 | 6.39 | 218.98 |
| 12.3 | 9.47 | 324.65 |
| 13.4 | 47.83 | 1639.59 |
| 13.9 | 31.01 | 1063.00 |
| 14.3 | 14.01 | 480.22 |
| 14.7 | 18.95 | 649.62 |
| 15.6 | 20.90 | 716.30 |
| 17.1 | 6.64 | 227.53 |
| 17.8 | 100.00 | 3428.04 |
| 19.0 | 7.07 | 242.48 |
| 19.3 | 8.25 | 282.66 |
| 20.0 | 2.45 | 84.08 |
| 21.2 | 11.00 | 377.11 |
| 22.0 | 19.74 | 676.56 |
| 23.6 | 64.54 | 2212.58 |
| 24.7 | 6.14 | 210.37 |
| 26.0 | 4.10 | 140.49 |
| 26.9 | 6.97 | 238.82 |
| 28.0 | 33.58 | 1151.04 |
| 32.3 | 1.40 | 47.83 |
| 35.9 | 0.92 | 31.62 |
| 38.7 | 0.95 | 32.55 |

Differential Scanning Calorimetry (DSC)

DSC data was collected on a TA Instruments Model Number Q2000 instrument with the following parameters:
  Sample size: approximately, 3 mg
  Pan: sealed aluminum pan
  Range: 25-230° C.
  Heating Rate: 2° C./min under nitrogen gas flow.

The DSC thermogram for Form β is provided in FIG. 5, showing a single endothermic event having a peak of 187° C. and onset of 185° C.

Thermogravimetric Differential Thermal Analysis (TG-DTA) TG-DTA data was collected as described above in Example 1 except that the measurement range for Form β was between 25 and 230° C. The endothermic peak was detected at 188.59° C., the extrapolated onset temperature was 186.68° C. and the weight loss was not observed in the range of 25 and 220° C. Data for Form β is shown in FIG. 8.

Solid State NMR

Solid state $^{13}$C NMR data was collected for Form β as described above in Example 1. The $^{13}$C NMR spectrum is provided in FIG. 11 showing peaks at: 16.5, 25.8, 26.5, 33.1, 34.8, 36.7, 38.8, 48.2, 53.4, 77.7, 79.5, 101.2, 102.6, 117.5, 120.6, 151.1, 154.3, and 166.1 ppm.

Example 3

Preparation and Characterization of Compound A, Form γ

Preparation 1

Compound A (2491.5 g, crystalline Form α), which had been passed through a sieve of 500 μm, was ground with a Spiral Jet Mill 100AS (manufactured by Hosokawa Micron Corporation) under the conditions below to give a ground product (2106.5 g) and Compound A (247.9 g) adhering to the nozzle-ring part.

Grinding Conditions

Gas used: nitrogen

Grinding nozzle: 1.5 mm in diameter×4

Ejector nozzle: 1.3 mm in diameter

Air pressure for grinding: 0.50 to 0.60 MPa

Air pressure for ejector: 0.50 to 0.60 MPa

Rate for supplying Compound A: 4 g/min

Compound A (100 g, 322 mmol) adhering to the nozzle-ring part was added to formamide (330 mL) under nitrogen, and a seed crystal (1.00 g of crystalline form γ which may have also contained some Form β of Compound A) was added to the mixture. The mixture was stirred at room temperature for 30 days. A crystalline precipitate was collected on a filter and washed with ethyl acetate (150 mL) twice. The resulting wet crystal was added to ethyl acetate (300 mL) under nitrogen and the mixture was stirred at room temperature for 30 minutes. A crystalline precipitate was collected on a filter and washed with ethyl acetate (150 mL) twice and dried under reduced pressure at 40° C. to give Compound A, crystalline Form γ (74.1 g, yield 74%).

Preparation 2

Compound A, Form α (containing a minor but undetermined amount of Form β), (100 mg, 0.322 mmol) was added to N,N-dimethylformamide (0.2 mL) and the mixture was stirred at room temperature for 6 days. A crystalline precipitate was collected on a filter. The collected wet crystalline material was dried under reduced pressure at room temperature for 18 hours to give a Compound A, Form γ (13.7 mg, yield 13.7%).

Characterization

X-Ray Powder Diffraction

The XRPD pattern for Form γ is shown in FIG. 3 and the corresponding data is provided below in Table 3-1. Instrument and data acquisition parameters are as described above in Example 1 for the characterization of Form α.

TABLE 3-1

| Diffraction angle [2θ (°)] | Relative intensity [%] | Diffraction intensity [cps] |
|---|---|---|
| 7.7 | 10.32 | 692.73 |
| 10.6 | 7.64 | 512.67 |
| 13.3 | 100.00 | 6709.91 |
| 13.9 | 14.17 | 951.02 |
| 15.2 | 79.93 | 5363.01 |
| 15.6 | 16.12 | 1081.78 |
| 16.5 | 14.81 | 993.47 |
| 17.7 | 52.89 | 3549.06 |
| 17.9 | 45.66 | 3063.89 |
| 19.0 | 26.13 | 1753.04 |
| 19.9 | 2.07 | 139.16 |
| 21.0 | 10.34 | 693.77 |
| 21.4 | 7.31 | 490.71 |
| 21.8 | 36.03 | 2417.29 |
| 22.8 | 3.79 | 254.11 |
| 23.1 | 27.25 | 1828.29 |
| 23.7 | 51.32 | 3443.62 |
| 24.1 | 9.91 | 665.12 |
| 24.3 | 6.86 | 460.35 |
| 24.7 | 2.39 | 160.44 |
| 25.1 | 9.88 | 663.01 |
| 26.0 | 1.44 | 96.76 |
| 27.1 | 5.51 | 369.82 |
| 27.4 | 2.94 | 197.55 |
| 28.1 | 34.39 | 2307.33 |
| 29.7 | 4.91 | 329.16 |
| 30.2 | 5.33 | 357.79 |
| 30.7 | 1.40 | 93.96 |
| 31.6 | 1.81 | 121.53 |
| 32.4 | 1.65 | 110.79 |
| 33.2 | 1.40 | 93.71 |
| 34.0 | 3.22 | 216.08 |
| 34.3 | 2.79 | 187.09 |
| 34.7 | 2.99 | 200.46 |
| 35.3 | 2.19 | 146.78 |
| 35.9 | 2.71 | 181.75 |
| 38.0 | 1.21 | 80.94 |
| 38.7 | 1.36 | 91.15 |
| 39.7 | 2.32 | 155.67 |

Differential Scanning Calorimetry (DSC)

DSC data was collected on a TA Instruments Model Number Q2000 instrument with the following parameters:

Sample size: approximately, 3 mg

Pan: sealed aluminum pan

Range: 25-230° C.

Heating Rate: 2° C./min under nitrogen gas flow.

The DSC thermogram for Form γ is provided in FIG. 6, showing a single endothermic event having a peak of 196° C. and onset of 196° C.

Thermogravimetric Differential Thermal Analysis (TG-DTA)

TG-DTA data was collected as described above in Example 1. The endothermic peak was detected at 198.68° C., the extrapolated onset temperature was 197.38° C. and the weight loss was not observed in the range of 25 and 220° C. Data for Form γ is shown in FIG. 9.

Solid State $^{13}$C NMR

Solid state $^{13}$C NMR data was collected for Form γ as described above in Example 1. The $^{13}$C NMR spectrum is provided in FIG. 12 showing peaks at: 16.9, 26.5, 32.9, 36.4, 48.1, 53.7, 78.6, 102.6, 116.4, 117.9, 121.5, 151.8, 154.6, and 162.9 ppm.

Example 4

Quantitation of Forms β and γ in Samples of Form α

Manufactured batches of Compound A, Form α, as well as ointment formulations containing Compound A, Form α, were tested for the presence of Forms β and γ. Using XRPD methods, Forms β and γ could be detected down to the 1 w/w % level.

Batches of Compound A, Form α, which were used for this analysis are presented in Table 4-1.

[Table 9]

TABLE 4-1

| Lot | Size |
|---|---|
| P | 22.40 kg |
| V | 19.15 kg |

Batches of ointment containing Compounds A, Form α, (3%) which were used for this analysis are presented in Table 4-2. RH refers to relative humidity. M refers to duration in months.

[Table 10]

TABLE 4-2

| Lot No. | Drug Substance Lot | Size | Storage Condition |
|---|---|---|---|
| 223-1A | P | 60.00 kg | 25° C./60% RH 18 M |
| 239-1A | P | 60.00 kg | Initial |
| 266-1 | V | 4.00 kg | 40° C./75% RH 6 M |
| 320 | V | 4.00 kg | Initial |

Forms β and γ were quantitated in the above batches and ointments using a PANalytical X'Pert PRO powder X-ray diffractometer operating under the following parameters:

TABLE 11

| | |
|---|---|
| Radiation | Cu-Kα$_1$/45 kV/40 mA |
| Counter Monochrometer | Graphite counter monochrometer |
| Scanning Range (Form β) | 9.5 to 12.5° |
| Scanning Range (Form γ) | 15.0 to 17.5° |
| Soller slit | 0.02 rad |
| Divergence slit | ½ |
| Anti-scatter slit | ½ |
| Mask | Mask Fixed 20 mm |
| Mode | Transmission |
| Optics | Focusing mirror |
| Sample holder | Insert transmission (Product No. 9430 018 18251) Transmission holder (Product No. 9430 018 18401) |
| Scan step time | 3000 sec |
| Scan step | 0.0008° or 0.0016° |
| Film | Mylar ™ film |

Test for Form β

Preparation of the Test Sample (Compound A, Form α, Drug Substance)

A portion of Compound A test sample was ground in an agate mortar to a fine powder. About 10 mg was mounted in the sample holder.

Preparation of the Test Sample (Ointment)

About 1 g of ointment test sample was suspended in 80 mL of n-hexane. The flask was stoppered and shaken vigorously for 30 seconds. The mixture was filtered by suction using quantitative filter paper (5B), the washed with 5 mL portions of n-hexane five times. About 10 mg of precipitate was mounted in the sample holder.

Preparation of the Standard Sample

To Compound A, Lot U (Form α), was added Lot P-3273-58 (Form β) to obtain final concentrations of 2, 5 and 10 w/w %, which were mixed using a mortar. About 10 mg was mounted in the sample holder.

Procedure

X-ray powder diffraction measurements were carried out on the test samples and standard samples according to the instrument setting and data acquisition parameters described above (see, X-ray Powder Diffraction Method, General Tests, Processes and Apparatus. The Japanese Pharmacopoeia, 17th ed., Apr. 1, 2016, English Edition, pp 79-83). Peak areas of the diffraction peak (at 10.6°) obtained from standard samples and the test sample were determined by automatic integration or manual integration. The amount (%) of Form β of the test sample was calculated using the calibration curve that is generated from the peak areas of the standard sample.

The X-ray powder diffraction patterns obtained from the standard sample containing 0%, 2%, 5% and 10% w/w of Form β are shown in FIG. 13.

Test for Form γ

Preparation of the Test Sample (Compound A, Form α, Drug Substance)

A portion of Compound A test sample was ground in an agate mortar to a fine powder. About 10 mg was mounted in the sample holder.

Preparation of the Test Sample (Ointment)

About 1 g of ointment test sample was suspended in 80 mL of n-hexane. The flask was stoppered and shaken vigorously for 30 seconds. The mixture was filtered by suction using quantitative filter paper (5B), the washed with 5 mL portions of n-hexane five times. About 10 mg of precipitate was mounted in the sample holder.

Preparation of the Standard Sample

To Lot U (Form α) was added Compound A Lot YKF56-28G (Form γ) to obtain final concentrations of 1, 2 and 5 w/w %, which was mixed using a mortar. About 10 mg was mounted in the sample holder.

Procedure

X-ray powder diffraction measurements were carried out on the test samples and standard samples according to the instrument setting and data acquisition parameters described above (see, X-ray Powder Diffraction Method, General Tests, Processes and Apparatus, The Japanese Pharmacopoeia, 17th ed., Apr. 1, 2016, English Edition, pp 79-83). Peak areas of the diffraction peak (at 16.6°) obtained from standard samples and the test sample were determined by automatic integration or manual integration. If the peak area of the test sample was not more than that of 1% standard sample, it was reported "Not more than 1%." If the peak area of the test sample was more than that of 1% standard sample and not more than that of 2% standard sample, it was reported "Not more than 2%." If the peak area of the test sample was more than that of 2% standard sample and not more than that of 5% standard sample, it was reported "Not more than 5%."

The X-ray Powder Diffraction Patterns obtained from the standard sample containing 0%, 1%, 2% and 5% w/w of Form γ are shown in FIG. 14.

Results

Quantitation results are summarized in Table 4-3. Compound A, Drug Substance Lot P and JTE-052 Ointment Lot No. 223-1A and Lot No. 239-1A, manufactured by Drug Substance Lot P, all contained measurable amounts of Form j.

[Table 12]

TABLE 4-3

| Lot | Drug Substance Lot No. | Storage Condition | Form β | Form γ |
|---|---|---|---|---|
| Lot P | — | — | 9.3% | ≤1% |
| Lot V | — | — | ≤ QL$^a$ | ≤1% |
| 223-1A | P | 25° C./60% RH 18 M | 6.4% | ≤1% |
| 239-1A | P | Initial | 7.9% | ≤1% |
| 266-1 | V | 40° C./75% RH 6 M | ≤QL | ≤1% |
| 320 | V | Initial | ≤QL | ≤1% |

QL: Quantity Limit = 1.12% was calculated according to QL = 10(σ/slope).

Example 5

Single Crystal X-Ray Data

Single crystal X-ray structures were obtained for Forms α, β and γ according to the below parameters. Crystal structure data is provided in Table 5-1.

For Form α, single crystal data was obtained with a Rayonix MX225HE detector and SPring-8 BL41XU beam line using irradiation wavelength 0.71068 Å.

For Forms β and γ, single crystal data was obtained with a DECTRIS PILATUS3 6M detector and SPring-8 BL41XU beam line using irradiation wavelength 0.71068 Å.

[Table 13]

TABLE 5-1

| | Crystal Form | | |
|---|---|---|---|
| | β | γ | α |
| Temp (° C.) | 100 | 100 | 100 |
| Space Group | P1 (#1) | P2$_1$ (#4) | P1 (#1) |
| Z value | 4 | 2 | 2 |
| Z' value | 4 | 1 | 2 |
| a (Å) | 8.043 | 8.095 | 7.8 |
| b (Å) | 11.371 | 8.017 | 8.6 |
| c (Å) | 16.522 | 11.459 | 11.5 |
| α (°) | 97.537 | 90 | 95.2 |
| β (°) | 94.541 | 95.663 | 99.0 |
| γ (°) | 90.294 | 90 | 93.9 |
| D$_{calc}$ (g/cm$^3$) | 1.381 | 1.393 | 1.356 |
| Volume (Å$_3$) | 1493.1 | 740 | 760 |
| R$_1$ (%) (<10%) | 7.49 | 6.28 | 9.51 |
| R$_{wp}$ (%) (<25%) | 23.01 | 17.29 | 24.72 |
| GOF (0.8-1.3) | 1.036 | 0.984 | 1.068 |

Example 6

Competition experiment between Forms α and β of Compound A

Forms α and β of Compound A were mixed with the ratio of 1:1 by weight, and 1-butanol (800 μL) was added to the mixture (80 mg). The resulted suspension was stirred at room temperature for 12 days. The resultant was filtered at the same temperature, and then dried under reduced pressure at room temperature for 19 hours. Diffraction angles 2θ and diffraction intensities were measured by powder X-ray diffractometry for Forms α and β of Compound A used, the 1:1-by-weight mixture of Forms α and β of Compound A before stirring, and the resulted crystals. The instrument and data acquisition parameters herein are the same as those described above for the characterization of Form α in Example 1. The spectra measured are shown in FIG. 15. The figure shows spectra for Form α of Compound A used, Form β of Compound A used, the 1:1-by-weight mixture of Forms α and β of Compound A before stirring, and the crystal obtained after stirring, from the bottom.

The diffraction intensity ratios were compared between before and after stirring for the 10.2° peak of diffraction angle 2θ of Form α and the 10.6° peak of diffraction angle 2θ of Form β. As shown in the following table, the diffraction intensity ratio of the peak from Form β to the peak from Form α after being stirred was increased compared to the ratio before being stirred.

TABLE 14

| | Diffraction intensity of 10.2° (Form α) [cps] | Diffraction intensity of 10.6° (Form β) [cps] | Ratio of diffraction intensities (Form β/Form α) |
|---|---|---|---|
| Before stirring | 601.66 | 225.88 | 0.38 |
| After stirring | 819.03 | 673.08 | 0.82 |

Example 7

Competition experiment between Forms α and γ of Compound A Forms α and γ of Compound A were mixed with the ratio of 1:1 by weight, and 1-butanol (1 mL) was added to the mixture (100 mg). The resulted suspension was stirred at room temperature for 11 days. The resultant was filtered at the same temperature. Diffraction angles 2θ and diffraction intensities were measured by powder X-ray diffractometry for Forms α and γ of Compound A used, the 1:1-by-weight mixture of Forms α and γ of Compound A before stirring, and the resulted crystals. The instrument and data acquisition parameters herein are the same as those described above for the characterization of Form α in Example 1. The spectra measured are shown in FIG. 16. The figure shows spectra for Form α of Compound A used, Form γ of Compound A used, the 1:1-by-weight mixture of Forms α and γ of Compound A before stirring, and the crystal obtained after stirring, from the bottom. The diffraction intensity ratios were compared between before and after stirring for the 10.2° peak of diffraction angle 2θ of Form α and the 10.7° peak of diffraction angle 2θ of Form γ. As shown in the following table, the diffraction intensity ratio of the peak from Form γ to the peak from Form α after being stirred was increased compared to the ratio before being stirred.

TABLE 15

| | Diffraction intensity of 10.2° (Form α) [cps] | Diffraction intensity of 10.7° (Form γ) [cps] | Ratio of diffraction intensities (Form γ/Form α) |
|---|---|---|---|
| Before stirring | 1116.69 | 371.13 | 0.33 |
| After stirring | 418.12 | 208.04 | 0.50 |

Example 8

Competition experiment between Forms β and γ of Compound A (1) Forms β and γ of Compound A were mixed with the ratio of 1:1 by weight, and formamide (1 mL) was added to the mixture (150 mg). The resulted suspension was stirred at room temperature for 1 day. The resultant was filtered at the same temperature.

(2) Forms β and γ of Compound A were mixed with the ratio of 1:1 by weight, and N,N-dimethylformamide (1 mL) was added to the mixture (150 mg). The resulted suspension was stirred at room temperature for 1 day. The resultant was filtered at the same temperature.

(3) Forms β and γ of Compound A were mixed with the ratio of 1:1 by weight, and dimethylsulfoxide (1 mL) was added to the mixture (800 mg). The resulted suspension was stirred at room temperature for 1 day. The resultant was filtered at the same temperature.

Diffraction angles 2θ and diffraction intensities were measured by powder X-ray diffractometry for Forms β and γ of Compound A used, the 1:1-by-weight mixture of Forms β and γ of Compound A before stirring, and the crystals obtained in the above (1), (2), and (3). The instrument and data acquisition parameters herein are the same as those described above for the characterization of Form α in Example 1. The spectra measured are shown in FIG. 17. The figure shows spectra for Form γ of Compound A used, Form β of Compound A used, the 1:1-by-weight mixture of Forms β and γ of Compound A before stirring, the crystal obtained from formamide, that from N,N-dimethylformamide, and that from dimethylsulfoxide, from the bottom. According to the results of the above (1), (2), and (3), the mixed crystals formed a γ-single crystal.

Example 9

Solubility Test

Each sample (i.e., Forms α, β, and γ of Compound A) was weighed to a 4-mL-volume glass vial. A test solution (3 mL) was added to the vial and the mixture was suspended. About 150 mg of the sample was weighed for the test solution of the 1st fluid for solubility test of The Japanese Pharmacopoeia and about 15 mg was weighed for the test solutions of the 2nd fluid for solubility test of The Japanese Pharmacopoeia and water. Each mixture was shaken with a constant temperature incubator shaker (manufactured by TAITEC) at 20° C. for 3 hours. After being shaken, the supernatant was filtered through a polytetrafluoroethylene disk filter (Millex-LG; manufactured by Millipore) with the 0.2-μm pore size and 4-mm diameter. The measurement was performed by high-performance liquid chromatography (HPLC). The results are shown in the following table.

TABLE 16

| Solvent | Form α (anhydrous form) | Form β | Form γ |
|---|---|---|---|
| Water | 2.6 mg/mL | 2.0 mg/mL | 1.5 mg/mL |
| JP 1st fluid for solubility test | 45.0 mg/mL | 39.1 mg/mL | 36.4 mg/mL |
| JP 2nd fluid for solubility test | 2.7 mg/mL | 2.1 mg/mL | 1.5 mg/mL |

JP 1st fluid for solubility test (The Japanese Pharmacopoeia): Dissolve 2.0 g of sodium chloride in 7.0 mL of hydrochloric acid, and add water to make 1000 mL. This solution was clear and colorless, and its pH was about 1.2.
JP 2nd fluid for solubility test (The Japanese Pharmacopoeia): Mix one volume water to one volume phosphate buffer solution, pH 6.8.

Form α showed the highest solubility in each solvent measured, while Form γ showed the lowest solubility in each solvent measured.

Example 10

Formulations

Examples of formulations comprising Compound A (e.g., as Form α, Form β, Form γ, or a mixture of any of the aforementioned) are provided below and are not intended to be limiting.

Formulation 1 (Preparation of Capsule)

1) Compound A 30 mg
2) Microcrystalline cellulose 10 mg
3) Lactose 19 mg
4) Magnesium stearate 1 mg 1), 2), 3) and 4) are mixed to fill a gelatin capsule.

Formulation 2 (Preparation of Tablet)

1) Compound A 10 g
2) Lactose 50 g
3) Cornstarch 15 g
4) Carmellose calcium 44 g
5) Magnesium stearate 1 g The whole amount of 1), 2) and 3) and 30 g of 4) are combined with water, dried in vacuo, and then granulated. The resulting granules are mixed with 14 g of 4) and 1 g of 5), and tableted by a tableting machine. Then, 1000 tablets are obtained where 10 mg of Compound A is comprised in each tablet.

Various modifications of the invention, in addition to those described herein, will be apparent to those skilled in the art from the foregoing description. Such modifications are also intended to fall within the scope of the appended claims. Each reference, including all patents, patent applications, and journal literature, cited in the present application is incorporated herein by reference in its entirety.

The invention claimed is:

1. A crystalline form of 3-((3S,4R)-3-methyl-6-(7H-pyrrolo[2,3-d]pyrimidin-4-yl)-1,6-diazaspiro[3.4] octan-1-yl)-3-oxopropanenitrile having an X-ray powder diffraction pattern comprising a characteristic peak, in terms of 2θ(°), at about 11.8.

2. The crystalline form of claim 1, wherein the X-ray powder diffraction pattern comprises one or more additional characteristic peaks, in terms of 2θ(°), selected from about 10.5, about 19.3, and about 22.0.

3. The crystalline form of claim 1, wherein the X-ray powder diffraction pattern comprises two or more additional characteristic peaks, in terms of 2θ(°), selected from about 7.8, about 10.5, about 13.4, about 13.9, about 17.8, about 19.3, about 22.0, about 23.6, and about 28.0.

4. A crystalline form of 3-((3S,4R)-3-methyl-6-(7H-pyrrolo[2,3-d]pyrimidin-4-yl)-1,6-diazaspiro[3 0.4] octan-1-yl)-3-oxopropanenitrile having a DSC thermogram which is characterized by an endothermic peak at about 186° C.

5. The crystalline form of any one of claims 1 and 2 to 4, having a purity of at least about 50%.

6. The crystalline form of any one of claims 1 and 2 to 4, having a purity of at least about 75%.

7. The crystalline form of any one of claims 1 and 2 to 4, having a purity of at least about 85%.

8. The crystalline form of any one of claims 1 and 2 to 4, having a purity of at least about 90%.

9. The crystalline form of any one of claims 1 and 2 to 4, having a purity of at least about 95%.

10. A composition of crystalline 3-((3S,4R)-3-methyl-6-(7H-pyrrolo[2,3-d]pyrimidin-4-yl)-1,6-diazaspiro[3.4]octan-1-yl)-3-oxopropanenitrile comprising Form α and Form β, wherein Form a is characterized as having an X-ray powder diffraction pattern comprising a characteristic peak, in terms of 2θ(°), at about 10.2, and wherein Form (3 is characterized as having an X-ray powder diffraction pattern comprising a characteristic peak, in terms of 2θ(°), at about 11.8.

11. The composition of claim 10 consisting essentially of Form α and Form β.

12. The composition of claim 10, wherein Form β is present in an amount of about 1 to about 50% w/w with respect to Form α.

13. The composition of claim 10, wherein Form β is present in an amount of about 1 to about 20% w/w with respect to Form α.

14. The composition of claim 10, wherein Form β is present in an amount of about 1 to about 10% w/w with respect to Form α.

15. The composition of claim 10, wherein Form β is present in an amount of about 1 to about 5% w/w with respect to Form α.

16. The composition of claim 10, further comprising Form γ, wherein Form γ is characterized as having an X-ray powder diffraction pattern comprising two or more peaks, in terms of 2θ(°), selected from about 16.5, about 17.7, about 21.4, about 21.8, and about 23.1.

17. A pharmaceutical composition comprising the crystalline form or composition of any one of claims 1, 2 to 5, and 10 to 16, and a pharmaceutically acceptable carrier.

18. The pharmaceutical composition of claim 17 which is suitable for oral, parenteral, pulmonary, local, or topical administration.

19. The pharmaceutical composition of claim 17 which is suitable for topical administration.

20. The pharmaceutical composition of claim 17 in the form of a tablet, capsule, pill, powder, or ointment.

21. The pharmaceutical composition of claim 17 in the form of a powder suitable for reconstitution in liquid for IV, IM, or SC administration.

22. The pharmaceutical composition of claim 17, comprising white soft paraffin, hard paraffin, squalene, or a mixture thereof.

23. A method for treating or preventing a disease selected from organ transplant rejection, graft versus host reaction after transplantation, autoimmune disease, allergic diseases, and chronic myeloproliferative disease, comprising administering to a mammal a therapeutically effective amount of the crystalline form or composition of any one of claims 1, 2 to 4, and 10 to 16.

24. A method for treating or preventing rheumatoid arthritis, psoriasis, alopecia areata, dry eye, atopic dermatitis, eczema, or hand eczema comprising administering to a mammal a therapeutically effective amount of the crystalline form or composition of any one of claims 1, 2 to 4, and 10 to 16.

* * * * *

UNITED STATES PATENT AND TRADEMARK OFFICE
CERTIFICATE OF CORRECTION

PATENT NO. : 11,339,181 B2
APPLICATION NO. : 16/470854
DATED : May 24, 2022
INVENTOR(S) : Yukihiro Kamiya et al.

Page 1 of 1

It is certified that error appears in the above-identified patent and that said Letters Patent is hereby corrected as shown below:

On the Title Page

Column 2, OTHER PUBLICATIONS
Line 16, delete "Tropics" and insert -- Topics --.
Line 18, delete "Hilfker," and insert -- Hilfiker, --.

Column 2, Item (57), ABSTRACT
Line 6, delete "thereof" and insert -- thereof, --.

In the Claims

Column 42
Claim 1, Line 45, delete "[3.4] octan" and insert -- [3.4]octan --.
Claim 1, Line 47, delete "2θ)(°)," and insert -- 2θ(°), --.
Claim 4, Line 59, delete "[3 0.4] octan" and insert -- [3.4]octan --.

Column 43
Claim 10, Line 8, delete "a" and insert -- α --.
Claim 10, Line 10, delete "(3" and insert -- β --.

Column 44
Claim 17, Line 2, delete "1, 2 to 5," and insert -- 1, 2 to 4, --.

Signed and Sealed this
Twelfth Day of July, 2022

Katherine Kelly Vidal
*Director of the United States Patent and Trademark Office*